(12) United States Patent
Seto et al.

(10) Patent No.: US 8,998,938 B2
(45) Date of Patent: Apr. 7, 2015

(54) FLUID EJECTION DEVICE, DRIVING METHOD OF FLUID EJECTION DEVICE, AND OPERATING INSTRUMENT

(75) Inventors: Takeshi Seto, Chofu (JP); Kazuo Kawasumi, Chino (JP); Yasuyoshi Hama, Shimosuwa-machi (JP); Hideki Kojima, Matsumoto (JP); Yasuhiro Ono, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 815 days.

(21) Appl. No.: 12/568,156

(22) Filed: Sep. 28, 2009

(65) Prior Publication Data

US 2010/0078495 A1    Apr. 1, 2010

(30) Foreign Application Priority Data

Oct. 1, 2008  (JP) ................. 2008-256092

(51) Int. Cl.
*A61B 17/32*    (2006.01)
*A61B 17/3203*  (2006.01)

(52) U.S. Cl.
CPC .................. *A61B 17/3203* (2013.01)

(58) Field of Classification Search
CPC ............... A61B 17/3203; A01G 25/09
USPC .......... 606/167, 27, 39; 239/1, 102.1; 604/48, 604/22, 131; 601/2, 3
See application file for complete search history.

(56) References Cited

U.S. PATENT DOCUMENTS

| | | | | |
|---|---|---|---|---|
| 4,596,575 A | * | 6/1986 | Rosenberg et al. | 604/891.1 |
| 5,255,669 A | * | 10/1993 | Kubota et al. | 601/3 |
| 5,993,378 A | * | 11/1999 | Lemelson | 600/109 |
| 2002/0193817 A1 | * | 12/2002 | Lal et al. | 606/169 |
| 2008/0086077 A1 | | 4/2008 | Seto et al. | |

FOREIGN PATENT DOCUMENTS

| JP | A-2005-152127 | 6/2005 |
|---|---|---|
| JP | A-2008-82202 | 4/2008 |

* cited by examiner

*Primary Examiner* — Tuan V Nguyen
*Assistant Examiner* — Tin Nguyen
(74) *Attorney, Agent, or Firm* — Oliff PLC

(57) ABSTRACT

A fluid ejection device includes: a fluid chamber whose capacity is variable; an inlet flow path and an outlet flow path communicating with the fluid chamber; a capacity changing unit which changes the capacity of the fluid chamber; a fluid supplying unit which supplies fluid to the inlet flow path; a fluid ejection opening disposed at an end of the outlet flow path opposite to an end communicating with the fluid chamber; a vibrating unit which vibrates a component in the vicinity of the fluid ejection opening; a vibration detecting unit which detects the level of vibration of the component in the vicinity of the fluid ejection opening; and an operation control unit which controls operation of the capacity changing unit based on the level of the vibration detected by the vibration detecting unit.

15 Claims, 18 Drawing Sheets

FLUID EJECTION DEVICE, DRIVING METHOD OF FLUID EJECTION DEVICE, AND OPERATING INSTRUMENT

Japanese Patent Application No. 2008-256092 filed on Oct. 1, 2008, is hereby incorporated by reference in its entirety.

BACKGROUND

1. Technical Field

The present invention relates to a fluid ejection device which ejects fluid at high speed, and more particularly to a fluid ejection device, a driving method of a fluid ejection device, and an operating instrument capable of controlling fluid ejection according to contact condition between an ejection target object and an ejection end.

2. Related Art

A fluid ejection device which opens or removes tissue of a living body by cutting has been proposed by the present inventors (see JP-A-2008-82202).

This fluid ejection device includes: a pulse generating unit which has a fluid chamber whose capacity is variable, inlet flow path and outlet flow path communicating with the fluid chamber, a capacity changing unit for changing the capacity of the fluid chamber according to supply of driving signals; a connection flow path which has one end communicating with the outlet flow path and the other end having a fluid ejection opening (nozzle) whose diameter is smaller than that of the outlet flow path; a connection flow pipe containing the connection flow path and having rigidity sufficient for transmitting pulse of fluid flowing from the fluid chamber to the fluid ejection opening; and a pressure generating unit which generates pressure for supplying fluid to the inlet flow path. The fluid ejection device supplies fluid to the inlet flow path with constant pressure produced by the pressure generating unit, and generates pulse by changing the capacity of the fluid chamber using the capacity changing unit to deliver fluid.

When the capacity of the fluid chamber of the fluid ejection device is not changed, fluid flows under the balanced condition between supply pressure produced by the pressure generating unit and fluid path resistance. In this condition, delivery of fluid from the nozzle is continuous at low speed, producing substantially no tissue cutting capability.

When the capacity of the fluid chamber is rapidly decreased, the pressure of the fluid chamber increases. In this condition, increase in the flow amount of fluid delivered from the outlet flow path is larger than decrease in the flow amount of fluid flowing into the fluid chamber from the inlet flow path. Thus, pulsed flow is generated in the connection flow path. This pressure change at the time of delivery is transmitted through the connection flow path pipe such that fluid can be ejected from the fluid ejection opening formed at the end of the nozzle at high speed.

By repeating this operation, fluid can be delivered by high-speed pulse jet. In this structure, starting and stopping at the speed of several msec. or lower can be achieved by contracting and expanding the fluid chamber using a piezoelectric element.

This technology is applicable to a fluid ejection device disclosed in another reference (see JP-A-2005-152127) proposed by the present inventors as ejection device requiring no pressure generating unit.

When the fluid ejection device in the related art discussed above is used as a water scalpel in an operation, the operation is performed with the nozzle almost closely attached to the affected part. Thus, when the nozzle ejecting fluid is separated from the affected part, liquid drops produced by the fluid ejection are scattered. In this case, there is a possibility that removed pieces of tissue containing cancer or the like are scattered around.

SUMMARY

It is an advantage of some aspects of the invention to provide a fluid ejection device, a driving method of a fluid ejection device, and an operating instrument capable of controlling fluid ejection operation according to contact condition between an ejection target object and an ejection end.

First Aspect

A first aspect of the invention is directed to a fluid ejection device including: a fluid chamber whose capacity is variable; an inlet flow path and an outlet flow path communicating with the fluid chamber; a capacity changing unit which changes the capacity of the fluid chamber; a fluid supplying unit which supplies fluid to the inlet flow path; a fluid ejection opening disposed at an end of the outlet flow path opposite to an end communicating with the fluid chamber; a vibrating unit which vibrates a component in the vicinity of the fluid ejection opening; a vibration detecting unit which detects the level of vibration of the component in the vicinity of the fluid ejection opening; and an operation control unit which controls operation of the capacity changing unit based on the level of the vibration detected by the vibration detecting unit.

According to this structure, the pressure inside the fluid chamber changes to produce pulsed flow when the capacity of the fluid chamber is varied by the capacity changing unit. Then, the pulsed flow passes through the outlet flow path to be ejected through the fluid ejection opening.

When the vibrating force is applied to the component in the vicinity of the fluid ejection opening by the vibrating unit, the component in the vicinity of the fluid ejection opening and the fluid ejection opening vibrate.

After the level of the vibration of the component in the vicinity of the fluid ejection opening is detected by the vibration detecting unit, the operation of the capacity changing unit is controlled by the operation control unit according to the detected level of the vibration.

When the vibrating fluid ejection opening contacts a fluid ejection target object or an object in the vicinity of the target object (such as liquid reservoir of ejected fluid), the levels of the vibrations of the fluid ejection opening and the component in the vicinity of the fluid ejection opening vary (decrease). Then, this change is detected by the vibration detecting unit.

Based on this detection, the operation control unit controls the operation of the capacity changing unit to prohibit capacity changing operation or decrease fluid ejecting force when the level of the vibration detected by the vibration detecting unit corresponds to the level obtained at the time when the fluid ejection opening contacts nothing, for example.

When the level of the vibration detected by the vibration detecting unit corresponds to the level obtained at the time when the fluid ejection opening contacts the ejection target object or the object in the vicinity of the ejection target object (smaller vibration than vibration at the time of non contact), the operation control unit controls the operation of the capacity changing unit to change the capacity, for example.

By this method, ejection operation can be prohibited or ejecting force can be decreased when the fluid ejection opening does not contact the ejection target object or the object in the vicinity of the ejection target object. Thus, ejection of fluid in an unexpected direction and scattering of substances cut thereby can be prevented when the fluid ejection opening is separated from the ejection target object or the object in the vicinity of the ejection target object by operation error or the like of a user (hereinafter referred to as operator as well).

It is preferable that the component in the vicinity of the fluid ejection opening vibrates when vibrating force is applied to the component, and that the level of the vibration of the component varies (decreases, for example) when the end portion containing the fluid ejection opening contacts an object (such as solid and liquid).

Second Aspect

A second aspect of the invention is directed to the fluid ejection device of the first aspect, wherein the component in the vicinity of the fluid ejection opening forms the fluid ejection opening.

According to this structure, the component forming the fluid ejection opening vibrates when the vibrating unit applies vibrating force to the component forming the fluid ejection opening.

When the vibration detecting unit detects the level of the vibration of the fluid ejection opening, the operation control unit controls the operation of the capacity changing unit based on the detected level of the vibration.

Third Aspect

A third aspect of the invention is directed to the fluid ejection device of the first aspect, wherein the fluid ejection device further includes: a suction pipe having a suction opening positioned in the vicinity of the fluid ejection opening and a passage through which an object sucked via the suction opening passes; and a sucking force giving unit which gives sucking force for sucking an object in the vicinity of the suction opening. The component in the vicinity of the fluid ejection opening forms the suction opening.

According to this structure, the object in the vicinity of the suction opening (such as fluid ejected from the fluid ejection opening and tissue pieces or other object cut or removed by fluid ejection) is sucked when sucking force is given by the sucking force giving unit. Then, the sucked object passes through the passage formed inside the suction pipe to be conveyed to a container for storing sucked object or the like.

When the vibrating unit applies vibrating force to the component forming the suction opening, the suction opening vibrates.

After the vibration detecting unit detects the level of the vibration of the suction opening, the operation control unit controls the operation of the capacity changing unit according to the detected level of the vibration.

When the vibrating suction opening contacts a fluid ejection target object or an object in the vicinity of the ejection target object (such as liquid reservoir of ejected fluid), the level of the vibration of the suction opening varies (decreases, for example). This change is detected by the vibration detecting unit.

Based on this detection, the operation control unit controls the operation of the capacity changing unit to prohibit capacity changing operation or decrease fluid ejecting force when the level of the vibration detected by the vibration detecting unit corresponds to the level obtained at the time when the suction opening contacts nothing, for example.

When the level of the vibration detected by the vibration detecting unit corresponds to the level obtained at the time when the suction opening contacts the ejection target object or the object in the vicinity of the ejection target object (smaller vibration than vibration at the time of non contact), the operation control unit controls the operation of the capacity changing unit to change the capacity, for example.

By this method, ejection operation can be prohibited or ejecting force can be decreased when the suction opening does not contact the ejection target object or the object in the vicinity of the ejection target object. Thus, ejection of fluid in an unexpected direction and scattering of substances cut thereby can be prevented when the suction opening and the fluid ejection opening are separated from the ejection target object or the object in the vicinity of the ejection target object by operation error or the like of the operator.

Moreover, when the fluid ejection device having this structure is used as water scalpel in an operation, for example, cut tissue pieces of a living body or delivered fluid can be sucked by the fluid ejection device. Thus, operation can be performed with preferable view secured.

Fourth Aspect

A fourth aspect of the invention is directed to the fluid ejection device of the first or second aspect, wherein: the vibrating unit has a vibrating force generating section which generates vibrating force for vibrating the fluid ejection opening; the vibration detecting unit has a vibration receiving section which receives vibration; and the vibrating force generating section and the vibration receiving section are provided on the outlet flow path.

According to this structure, vibrating force applied to the outlet flow path using the vibrating force generating section vibrates the fluid ejection opening or the component in the vicinity of the fluid ejection opening. This vibration is received by the vibration receiving section.

Fifth Aspect

A fifth aspect of the invention is directed to the fluid ejection device of the fourth aspect, wherein: a flat surface is provided at least on a part of the outer circumferential surface of the outlet flow path; and the vibrating force generating section and the vibration receiving section are provided on the flat surface.

According to this structure, the vibrating force generating section and the vibration receiving section formed by material difficult to be bended can be easily attached to the outlet flow path while maintaining straight shapes.

Sixth Aspect

A sixth aspect of the invention is directed to the fluid ejection device of the third aspect, wherein: the vibrating unit has a vibrating force generating section which generates vibrating force for vibrating the suction opening; the vibration detecting unit has a vibration receiving section which receives vibration; and the vibrating force generating section and the vibration receiving section are provided on the suction pipe.

According to this structure, vibrating force applied to the suction pipe by the vibrating force generating section vibrates the suction opening. This vibration is received by the vibration receiving section.

Seventh Aspect

A seventh aspect of the invention is directed to the fluid ejection device of the sixth aspect, wherein: a flat surface is provided at least on a part of the outer circumferential surface of the suction pipe; and the vibrating force generating section and the vibration receiving section are provided on the flat surface.

According to this structure, the vibrating force generating section and the vibration receiving section formed by material difficult to be bended can be easily attached to the suction pipe while maintaining straight shapes.

Eighth Aspect

An eighth aspect of the invention is directed to the fluid ejection device of any of fourth through seventh aspects, wherein the vibration receiving section has a distortion gauge.

According to this structure, the level of vibration can be easily detected by the distortion gauge.

Ninth Aspect

A ninth aspect of the invention is directed to the fluid ejection device of any of the fourth through eighth aspects, wherein the vibrating force generating section has a piezoelectric element.

According to this structure, vibrating force is generated by the piezoelectric element. Thus, vibrating force can be easily controlled by controlling applied voltage.

Tenth Aspect

A tenth aspect of the invention is directed to the fluid ejection device of the eighth aspect, wherein the vibrating force generating section has function of generating vibrating force and function of receiving vibration as the vibration receiving section by using the piezoelectric element for generating vibrating force.

According to this structure, both generation of vibrating force and reception of vibration are achieved by one piezoelectric element. Thus, the vibrating unit and the vibration detecting unit can be manufactured at relatively low cost.

Eleventh Aspect

An eleventh aspect of the invention is directed to the fluid ejection device of the tenth aspect, wherein: the vibrating unit has a drive section which drives the piezoelectric element; the vibration detecting unit has an electromotive force detecting section which detects electromotive force generated on the piezoelectric element; and a time division control unit which controls the drive section and the electromotive force detecting section such that supply of drive signals by the drive section and detection of electromotive force by the electromotive force detecting section are performed by time division is provided.

According to this structure, both, generation of vibrating force and reception of vibration are achieved by one piezoelectric element. Thus, the vibrating unit and the vibration detecting unit can be manufactured at relatively low cost.

Twelfth Aspect

A twelfth aspect of the invention is directed to the fluid ejection device of any of the fourth through eleventh aspects, wherein: the vibrating unit has the plural vibrating force generating sections; and the vibrating unit controls operations of the vibrating force generating sections such that forces generated by the plural vibrating force generating sections can increase the vibrating force.

According to this structure, larger vibrating force is generated. Thus, an object to be vibrated can be greatly vibrated, and the detection accuracy of the level of vibration can be increased.

Thirteenth Aspect

A thirteenth aspect of the invention is directed to the fluid ejection device of any of the first through twelfth aspects, wherein the operation control unit allows operation of the capacity changing unit when the level of vibration detected by the vibration detecting unit is lower than a predetermined level, and prohibits operation of the capacity changing unit when the level of the vibration is equal to or higher than the predetermined level.

According to this structure, fluid ejection is executed when the fluid ejection opening or the suction opening contacts the ejection target object or the object in the vicinity of the fluid target object. When the fluid ejection opening or the suction opening does not contact the ejection target object or the object in the vicinity of the fluid target object, ejection is prohibited.

Fourteenth Aspect

A fourteenth aspect of the invention is directed to a driving method of a fluid ejection device comprising: the fluid ejection device including a fluid chamber whose capacity is variable, an inlet flow path and an outlet flow path communicating with the fluid chamber, a capacity changing unit which changes the capacity of the fluid chamber, a fluid supplying unit which supplies fluid to the inlet flow path, a fluid ejection opening disposed at an end of the outlet flow path opposite to an end communicating with the fluid chamber, a vibrating unit, a vibration detecting unit, and an operation control unit; vibrating a component in the vicinity of the fluid ejection opening by the vibrating unit; detecting the level of vibration of the component in the vicinity of the fluid ejection opening by the vibration detecting unit; and controlling operation of the capacity changing unit based on the level of the vibration detected in the vibration detecting step by the operation control unit.

According to this method, operations and advantages similar to those of the fluid ejection device of the first aspect can be offered.

Fifteenth Aspect

A fifteenth aspect of the invention is directed to an operating instrument which supports medical treatment for an affected portion by using ejection of fluid, including the fluid ejection device of any of the first through thirteenth aspects.

According to this structure, medical treatment for cutting and removing an affected portion such as tumor can be supported by the ejection of fluid provided by the fluid ejection device described above.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment according to an aspect of the invention is hereinafter described with reference to the drawings. FIGS. 1 through 9 show a fluid ejection device, a driving method of the fluid ejection device, and an operating instrument according to the first embodiment.

The fluid ejection device according to an aspect of the invention can be used for various applications such as drawing by ink or the like, cleaning of minute object and structure, cutting and removal of objects, and operation scalpels. In this embodiment, a water pulse scalpel (fluid ejection device and operating instrument) appropriately used for opening or removing tissue of a living body by cutting will be described as an example. Thus, fluid used in this embodiment is water, physiological salt water, liquid medicine or the like.

Figure 1:
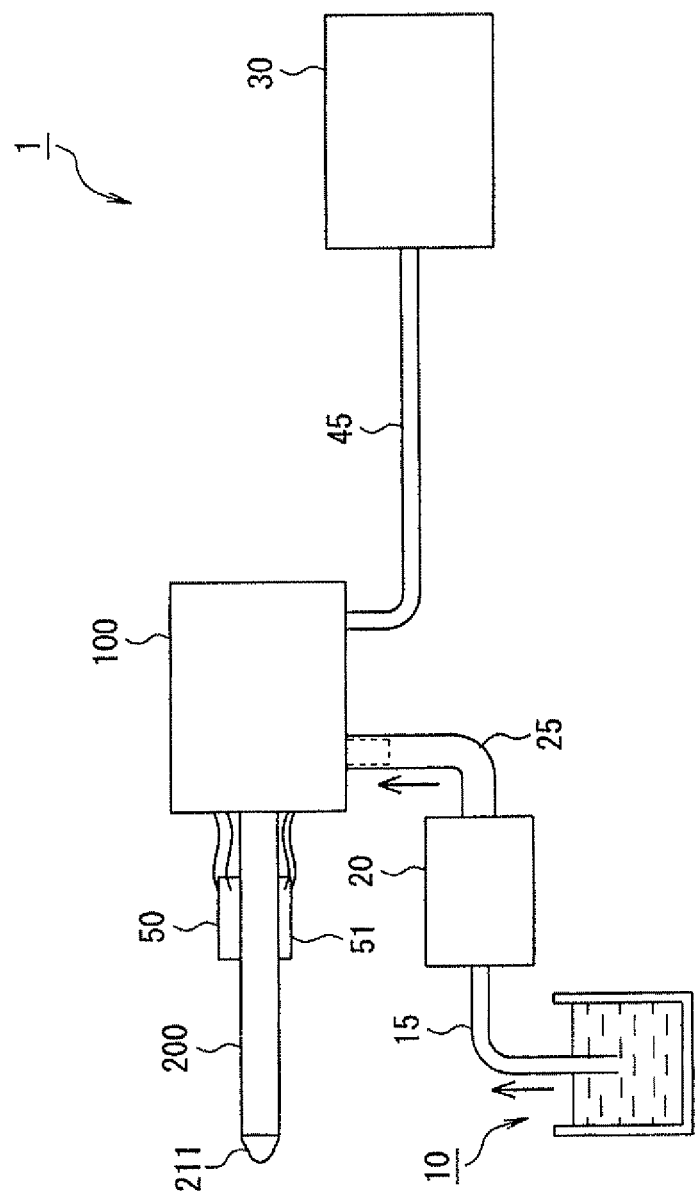
FIG. 1 illustrates a general structure of a fluid ejection device according to the invention.

Initially, the structure of the fluid ejection device according to this embodiment is explained with reference to FIG. 1. FIG. 1 illustrates a general structure of a fluid ejection device 1 according to this embodiment.

As illustrated in FIG. 1, the fluid ejection device 1 has a basic structure including a fluid container 10 for storing fluid, a pump 20 as a pressure generating unit, a pulse generating unit 100 for generating pulsed flow of fluid received from the pump 20, a drive unit 30 for driving the pulse generating unit 100, a vibration generating piezoelectric element 50, and a distortion gauge 51.

The pulse generating unit 100 is connected with a pipe-shaped narrow connection flow path pipe 200. A nozzle 211 having a smaller diameter than the flow path diameter of the connection flow path pipe 200 is inserted into the end of the connection flow path pipe 200.

The vibration generating piezoelectric element 50 for vibrating the nozzle 211 (hereinafter abbreviated as piezoelectric element 50), and the distortion gauge 51 for detecting the level of vibration generated on the nozzle 211 are fixed to the outer circumferential surface of the connection flow path pipe 200.

Passages for two supply lines VPZT(−) and VPZT(+) for supplying drive signals to the piezoelectric element 50, gauge input line and gauge output line of the distortion gauge 51, and two supply lines JPZT(−) and JPZT(+) for supplying drive signals to a fluid ejecting piezoelectric element 401 (described later) are formed inside the pulse generating unit 100.

These passages are joined at the exit of signal lines extended from the pulse generating unit 100, and the four supply lines and the gauge input line and the gauge output line are collectively extended from one exit position to the outside.

These lines are collected by a cable 45, and connected with the drive unit 30. The respective lines of the cable 45 are electrically connected with the corresponding components of the drive unit 30.

The flow of fluid in the fluid ejection device 1 is now briefly described with reference to FIGS. 1 and 2.

Figure 2:
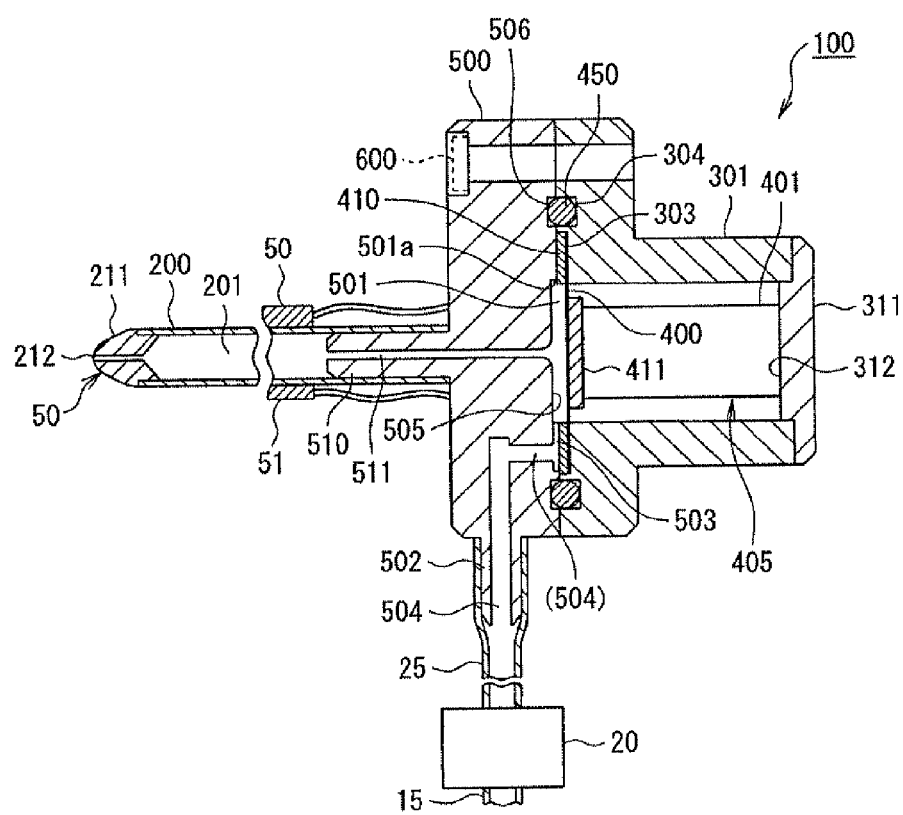
FIG. 2 is a cross-sectional view of a structure of a pulse generating unit according to the invention.

FIG. 2 is a cross-sectional view showing the structure of the pulse generating unit 100 in this embodiment. In FIG. 2, the left-right direction corresponds to the up-down direction. FIG. 2 is a cross-sectional view taken along a line A-A' in FIG. 4.

The fluid stored in the fluid container 10 is sucked through a connection tube 15 using the pump 20, and supplied to the pulse generating unit 100 via a connection tube 25 with constant pressure. The pulse generating unit 100 has a fluid chamber 501, and a capacity changing unit 405 for changing the capacity of the fluid chamber 501 according to drive signals sent from the drive unit 30. The pulse generating unit 100 generates pulse by operation of the capacity changing unit 405, and ejects fluid at high speed through the connection flow path pipe 200 and the nozzle 211. The details of the pulse generating unit 100 will be explained later.

Pressure is not required to be generated by using the pump 20 but may be produced by supporting a liquid carry bag at a position higher than the pulse generating unit 100 using a stand or the like. In this case, the pump 20 can be eliminated, and advantages such as simplification of the structure and easy disinfection can be provided.

The delivery pressure of the pump 20 is set at about 3 atm. (0.3 MPa) or lower. When the liquid carry bag is used, the pressure corresponds to the height difference between the pulse generating unit 100 and the liquid level of the liquid carry bag. It is preferable that the height difference is so determined as to produce pressure in the range from 0.1 to 0.15 atm. (0.01 to 0.15 MPa) when the liquid carry bag is used.

While performing operation using the fluid ejection device 1, the operator holds the pulse generating unit 100. In this case, it is preferable that the connection tube 25 extending to the pulse generating unit 100 is flexible as much as possible. Accordingly, the connection tube 25 is preferably a flexible and narrow tube which produces the lowest possible pressure sufficient for supplying liquid to the pulse generating unit 100.

Particularly when failure of the device leads to serious accidents in such cases as brain operation, ejection of high-pressure fluid caused by cutting of the connection tube 25 or the like must be avoided. For this reason, the pressure of the connection tube 25 is required to be kept low.

The structure of the pulse generating unit 100 is now discussed with reference to FIGS. 2 through 4.

Figure 3:
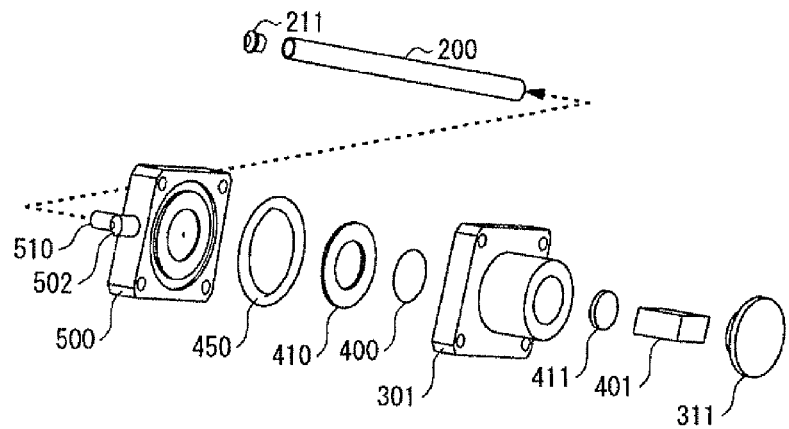
FIG. 3 illustrates a disassembled fluid ejection part of the fluid ejection device.

FIG. 3 illustrates a disassembled fluid ejection area of the fluid ejection device 1. FIG. 4 is a plan view showing an inlet flow path 503 on an upper case 500 as viewed from a junction surface connected with a lower case 301.

Figure 4:
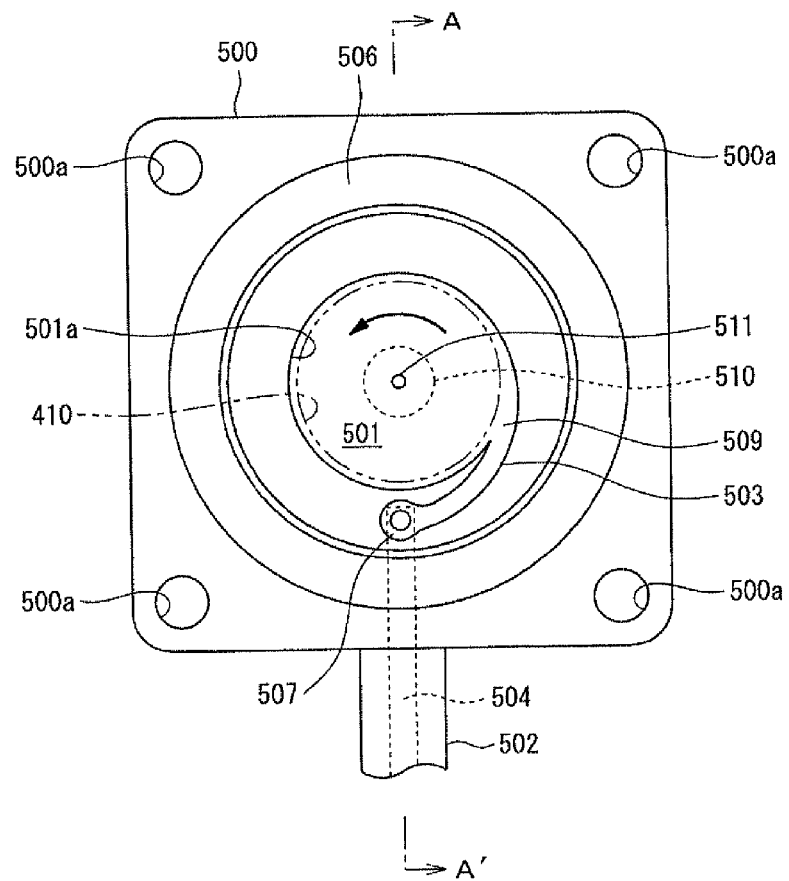
FIG. 4 is a plan view of an inlet flow path.

As illustrated in FIGS. 2 through 4, the pulse generating unit 100 includes the upper case 500 having screw holes 500a at the four corners, and the lower case 301 having screw holes 301a (not shown) at the four corners. The upper case 500 and the lower case 301 are joined such that the corresponding screw holes 500a and 301a are opposed to one another on the junction surfaces, and fixed to each other by inserting four fixing screws 600 (not shown) into the screw holes 500a and 301a.

The lower case 301 is a hollow cylindrical component having a fringe portion, and one end of the lower case 301 is closed by a bottom plate 311. A piezoelectric element 401 as one of the components constituting the capacity changing unit 405 is provided in the space inside the lower case 301.

The piezoelectric element 401 is a lamination type piezoelectric element constituting an actuator. One end of the piezoelectric element 401 is fixed to a diaphragm 400 via an upper plate 411, and the other end is fixed to an upper surface 312 of the bottom plate 311.

The diaphragm 400 is formed by a disk-shaped metal thin plate, and the circumferential area of the diaphragm 400 is disposed within an annular concave 303 formed on the upper surface of the lower case 301 to be closely fixed to the bottom surface of the concave 303. A reinforcing plate 410 formed by disk-shaped metal thin plate and having a circular opening at the center is laminated on the upper surface of the diaphragm 400.

According to this structure, the piezoelectric element 401 expands and contracts in response to drive signals inputted to the piezoelectric element 401 (operation voltage applied) from the drive unit 30. Then, the upward force at expansion and the downward force at contraction move the upper plate 411 in the up-down direction. By movement of the upper plate 411, the diaphragm 400 deforms and changes the capacity of the fluid chamber 501.

Thus, the capacity changing unit 405 is constituted by the piezoelectric element 401, the upper plate 411, the diaphragm 400, and the reinforcing plate 410.

The upper case 500 has a circular concave at the center of the surface opposed to the lower case 301. The fluid chamber 501 corresponds to a rotation body formed by this circular concave and the diaphragm 400 and filled with fluid inside. Thus, the fluid chamber 501 is a space surrounded by a sealing surface 505 and an inner circumferential side wall 501a of the concave of the upper case 500 and the diaphragm 400. An outlet flow path 511 is formed substantially at the center of the fluid chamber 501.

The outlet flow path 511 extends from the fluid chamber 501 to the end of the outlet flow path pipe 510 projecting from one end surface of the upper case 500. The connecting portion between the outlet flow path 511 and the sealing surface 505 of the fluid chamber 501 is smoothly rounded to reduce fluid resistance.

While the shape of the fluid chamber 501 in this embodiment has a substantially cylindrical shape with both ends sealed, the shape may be conical, trapezoidal, semispherical in the side view, or any arbitrary shapes. When the connecting portion between the outlet flow path 511 and the sealing surface 505 is funnel-shaped, for example, bubbles in the fluid chamber 501 as will be described later can be easily discharged.

The connection flow path pipe 200 is connected with the outlet flow path pipe 510. The connection flow path pipe 200 has a connection flow path 201 whose diameter is larger than that of the outlet flow path 511. The thickness of the pipe of the connection flow path pipe 200 is set in such a range that the connection flow path pipe 200 has rigidity sufficient for absorbing no pressure pulse of fluid.

The nozzle 211 is inserted into the end of the connection flow path pipe 200. The nozzle 211 has a fluid ejection opening 212. The diameter of the fluid ejection opening 212 is smaller than that of the connection flow path 201.

The piezoelectric element 50 and the distortion gauge 51 are fixed to the outer circumferential surface of the connection flow path 200 at positions opposed to each other with the connection flow path 200 disposed therebetween and positions shifted to the end from the connection portion between the outlet flow path pipe 510 and the connection flow path 200 on the pulse generating unit 100 side.

An inlet flow path pipe 502 to which the connection tube 25 for supplying fluid from the pump 20 is attached is formed on the side surface of the upper case 500. The inlet flow path pipe 502 has an inlet flow path side connection flow path 504. The connection flow path 504 communicates with the inlet flow path 503. The inlet flow path 503 is formed on the periphery of the sealing surface 505 of the fluid chamber 501 in the shape of groove, and communicates with the fluid chamber 501.

A packing box 304 on the lower case 301 side and a packing box 506 on the upper case 500 side are provided on the junction surface between the upper case 500 and the lower case 301 at positions away from the diaphragm 400 in the outer circumferential direction. Also, a ring-shaped packing 450 is inserted into the space formed by the packing boxes 304 and 506.

When the upper case 500 and the lower case 301 are assembled, the periphery of the diaphragm 400 and the periphery of the reinforcing plate 410 are brought into close contact with each other by the periphery of the sealing surface 505 of the upper case 500 and the bottom surface of the concave 303 of the lower case 301. In this case, the packing 450 is pressed by the upper case 500 and the lower case 301 to prevent fluid leakage from the fluid chamber 501.

The inside space of the fluid chamber 501 has high pressure such as 30 atm. (3 MPa) or higher at the time of fluid delivery. In this case, there is a possibility of slight leakage of fluid through the connecting portions of the diaphragm 400, the reinforcing plate 410, the upper case 500, and the lower case 301. However, such leakage can be prevented by the function of the packing 450.

The packing 450 disposed as illustrated in FIG. 2 is compressed by pressure of fluid leaking from the fluid chamber 501 with high pressure, and further strongly pressed by the inside walls of the packing boxes 304 and 506. Thus, leakage of fluid can be more securely prevented. Accordingly, high pressure increase inside the fluid chamber 501 can be maintained during operation.

The inlet flow path 503 formed on the upper case 500 is now explained in more detail.

As illustrated in FIG. 4, the inlet flow path 503 has a groove formed on the periphery of the sealing surface 505 of the upper case 500 and the reinforcing plate 410 fixed to the sealing surface 505 with pressure.

One end of the inlet flow path 503 communicates with the fluid chamber 501, and the other end communicates with the connection flow path 504. A fluid reservoir 507 is provided on the connection portion between the inlet flow path 503 and the connection flow path 504. The connection portion between the fluid reservoir 507 and the inlet flow path 503 is smoothly rounded to reduce fluid resistance.

The inlet flow path 503 communicates with the inner circumferential side wall 501a of the fluid chamber 501 substantially in the tangential direction. The fluid supplied from the pump 20 with constant pressure flows along the inner circumferential side wall 501a (in the direction indicated by an arrow in the figure) to generate rotational flow in the fluid chamber 501. Bubbles having low density and contained in the fluid chamber 501 gather at the center of the rotational flow due to centrifugal force of the rotational flow.

The bubbles gathered at the center are discharge through the outlet flow path 511. Thus, it is preferable that the outlet flow path 511 is disposed in the vicinity of the center of the rotational flow, that is, the axial center of the rotation body. According to the example shown in FIG. 4, the shape of the inlet flow path 503 in the plan view is curved in spiral shape. The inlet flow path 503 may have a linear shape communicating with the fluid chamber 501, but is curved in this embodiment so as to obtain desired inertance in the narrow space by increasing the flow path length of the inlet flow path 503.

As illustrated in FIG. 2, the reinforcing plate 410 is provided between the diaphragm 400 and the periphery of the sealing surface 505 on which the inlet flow path 503 is formed. The reinforcing plate 410 is provided for the purpose of increasing durability of the diaphragm 400. Since a notch-shaped connection opening 509 is formed on the connecting portion between the inlet flow path 503 and the fluid chamber 501, it is considered that fatigue breakage is caused by stress concentration in the vicinity of the connection opening 509 when the diaphragm 400 is operated at high frequency. Thus, the reinforcing plate 410 having continuous opening without notch is provided to prevent stress concentration generated on the diaphragm 400.

According to the fluid ejection device 1 having this structure, the screw holes 500a are formed at the four corners of the outer periphery of the upper case 500 such that the upper case 500 and the lower case 301 can be connected with each other by screws inserted into the screw holes 500a. However, the reinforcing plate 410 and the diaphragm 400 may be connected and fixed to one another in lamination as one piece unit, for example, though not shown in the figure. The reinforcing plate 410 and the diaphragm 400 may be fixed by adhesive, fixed layer diffused junction, welding or other fixing methods. It is preferable that the reinforcing plate 410 and the diaphragm 400 are closely connected with each other via the junction surface.

According to the fluid ejection device 1 having this structure, the outlet flow path 511 and the nozzle 211 are connected with each other via the connection flow path pipe 200. However, the nozzle 211 may be inserted into the end of the outlet flow path pipe 510 on the side opposite to the fluid chamber 501 without using the connection flow path pipe 200. In this case, the structure can be further simplified.

When the fluid ejection device 1 is used in operation, it is preferable that the connection flow path pipe 200 is used so as to appropriately increase the distance between a handpiece and the fluid ejection opening 212 (to be a length capable of reaching a deeper affected part).

The principle of the fluid delivery performed by the pulse generating unit 100 according to this embodiment is now discussed.

The fluid delivery by the pulse generating unit 100 in this embodiment is achieved by the difference between inlet flow path side inertance L1 (referred to as synthetic inertance L1 as well) and outlet flow path side inertance L2 (referred to as synthetic inertance L2 as well).

Initially, the details of inertance are explained.

Inertance L is expressed as $L=\rho \times h/S$ ($\rho$: density of fluid, S: cross-sectional area of flow path, h: length of flow path). By transforming the equation of motion in the flow path by using the inertance L, the relation $\Delta P = L \times dQ/dt$ is obtained ($\Delta P$: pressure difference in flow path, Q: flow amount of fluid flowing in flow path).

Thus, the inertance L indicates effect level for flow amount change with time. The flow amount change with time decreases as the inertance L becomes larger, but increases as the inertance L becomes smaller.

In case of synthetic inertance in parallel connection of plural flow paths or in serial connection of plural flow paths having different shapes, synthetic inertance can be calculated by combining inertance of each flow path similarly to inductance in parallel connection or serial connection of electric circuit.

Since the diameter of the connection flow path 504 is sufficiently larger than that of the inlet flow path 503, only the inertance of the inlet flow path 503 needs to be calculated as the inertance L1 on the inlet flow path side. Since the connection tube for connecting the pump 20 and the inlet flow path and has flexibility, the inertance of the connection tube is excluded from the calculation of the inertance L1.

The diameter of the connection flow path 201 is considerably larger than that of the outlet flow path, and the pipe portion (pipe wall) of the connection flow pipe 200 has only a small effect on the inertance L2 on the outlet flow path side when the thickness of the pipe portion of the connection flow pipe 200 is small. Thus, the inertance L2 on the outlet flow path side can be replaced with the inertance of the outlet flow path 511.

When the thickness of the pipe wall of the connection flow path pipe 200 is large, the inertance L2 becomes the synthesis inertance of the outlet flow path 511, the connection flow path 201, and the nozzle 211.

In this embodiment, the flow path length and the cross-sectional area of the inlet flow path 503 and the flow path length and the cross-sectional area of the outlet flow path 511 are determined such that the inertance L1 on the inlet flow path side becomes larger than the inertance L2 on the outlet flow path side.

The detailed structure of the drive unit 30 is now described with reference to FIG. 5.

Figure 5:
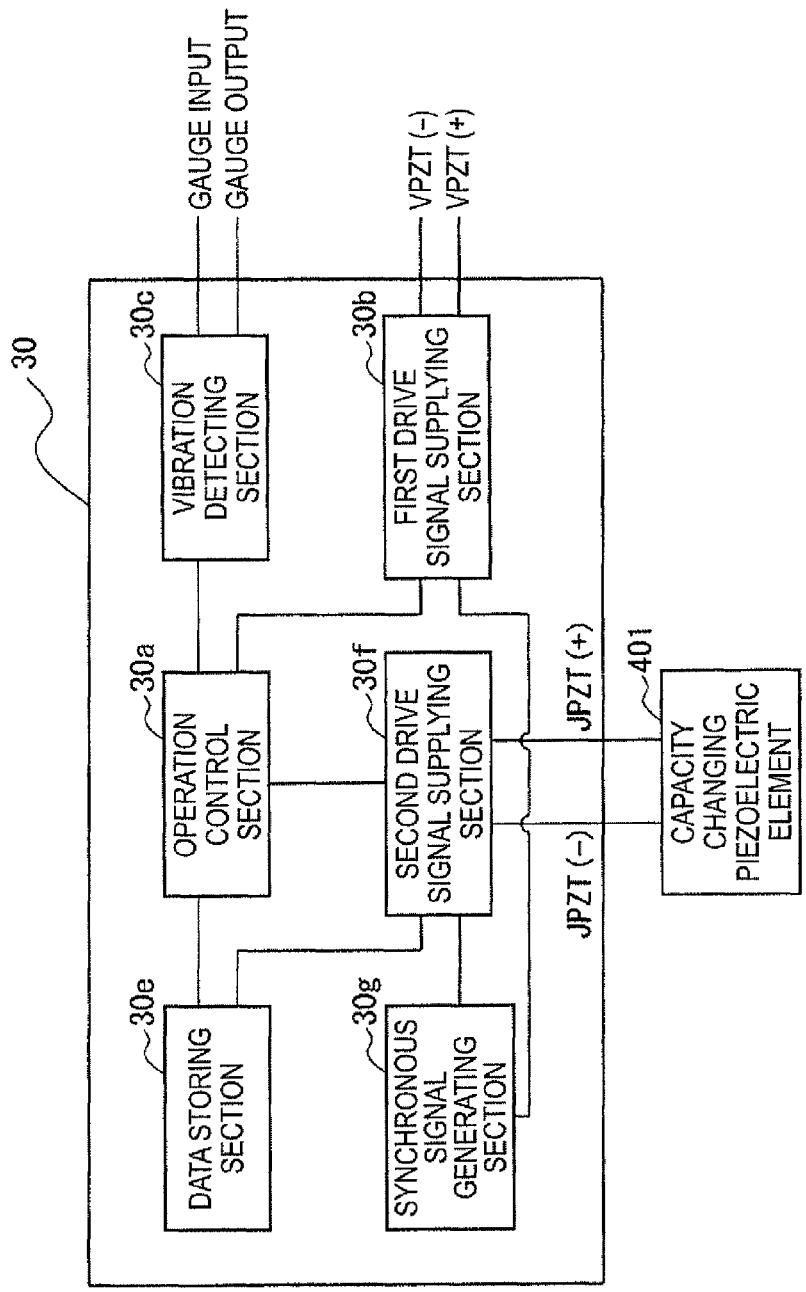
FIG. 5 is a block diagram showing a detailed structure of a drive unit.

FIG. 5 is a block diagram showing the detailed structure of the drive unit 30.

As shown in FIG. 5, the drive unit 30 includes an operation control section 30a, a first drive signal supplying section 30b, a vibration detecting section 30c, a data storing section 30e, a second drive signal supplying section 30f, and a synchronous signal generating section 30g.

The operation control section 30a has function of issuing operation commands to the respective components in response to operation input given through an input unit (not shown) of the fluid ejection device 1. The operation control section 30a provides function of controlling various operation processes such as process for supplying drive signals from the first drive signal supplying section 30b, process for determining contact condition of the nozzle 211, and process for supplying drive signals from the second drive signal supplying section 30f.

More specifically, the operation control section 30a outputs vibration generating command which requests the connection flow path pipe 200 to generate vibrating force for vibrating the nozzle 211 to the first drive signal supplying section 30b when the drive switch (not shown) of the water pulse scalpel is switched to ON from OFF.

By this step, the piezoelectric element 50 expands and contracts in response to the drive signals supplied from the first drive signal supplying section 30b to produce vibrating force. Then, this vibrating force is transmitted to the connection flow path 200 and the nozzle 211 to vibrate the connection flow path pipe 200 and the nozzle 211.

The operation control section 30a determines whether the nozzle 211 contacts the affected portion or an object in the vicinity of the affected portion (such as ejected fluid reservoir) based on the detection result of the vibration level received from the vibration detecting section 30c (output voltage of the distortion gauge 51) and the threshold of the vibration level stored in the data storing section 30e. When it is determined that the nozzle 211 contacts the affected portion or the object, the operation control section 30a issues ejection driving command for performing fluid ejection to the second drive signal supplying section 30f.

By this step, the second drive signal supplying section 30f supplies drive signals to the piezoelectric element 401 to expand and contract the piezoelectric element 401. Then, the fluid chamber 501 thus contracted compresses fluid inside the fluid chamber 501 to generate pulsed flow to be ejected through the fluid ejection opening 212 via the output flow path 511 and the connection flow path 201.

When it is determined that the nozzle 211 does not contact the affected portion or the object, the operation control section 30a does not output ejection driving command or outputs ejection stop command during ejection of fluid (during operation of piezoelectric element 401).

When the drive switch of the water pulse scalpel is switched from ON to OFF, the operation control section 30a issues ejection stop command for stopping fluid ejection to the second drive signal supplying section 30f. Then, the operation control section 30a outputs vibration stop command for suspending vibration of the nozzle 211 to the first drive signal supplying section 30b.

By this step, fluid ejection and vibration of the nozzle 211 stop.

The first drive signal supplying section 30b has function of supplying drive signals for generating vibration to the piezoelectric element 50 in synchronization with synchronous signals from the synchronous signal generating section 30g in response to vibration generating command received from the operation control section 30a.

More specifically, the first drive signal supplying section 30b reads corresponding vibration generation waveform information (digital waveform data) from the data storing section 30e based on waveform specifying information contained in the vibration generating command, produces analog drive signals converted from the digital waveform information read from the data storing section 30e, and supplies the drive signals thus produced to the piezoelectric element 50 in synchronization with the synchronous signals. The waveform specifying information is identification information or the like attached to the vibration generation signal waveform.

The first drive signal supplying section 30b further has function of stopping drive signal supply in response to the drive signal vibration stop command received from the operation control section 30a.

According to this embodiment, supply of drive signals is stopped after supply of final waveform in one cycle being supplied to the piezoelectric element 50 when the stop command is inputted from the operation control section 30a during supply of drive signals.

The vibration detecting section 30c includes a detection circuit having Wheatstone bridge circuit to detect resistance change of the distortion gauge 51 resulting from bending change of the connection flow path pipe 200 caused by vibrating force given from the piezoelectric element 50 as voltage level by using the detection circuit. Then, the vibration detecting section 30c outputs the detection level (voltage) as the detection result to the operation control section 30a.

The data storing section 30e includes a storage medium for storing waveform information about plural types of signal waveforms corresponding to the set ejection intensity and having different cycles and amplitudes, thresholds for contact detection, data used for processes performed by the respective parts, and others. The data storing section 30e reads data stored in the storing medium in response to reading requests from the respective parts, and writes the data to the storing medium in response to writing requests from the respective parts.

The second drive signal supplying section 30f has function of supplying drive signals to the piezoelectric element 401 of the capacity changing unit 405 through the supply lines JPZT (−) and JPZT(+) in synchronization with synchronous signals from the synchronous signal generating section 30g in response to the ejection driving command issued from the operation control section 30a.

More specifically, the second drive signal supplying section 30f reads corresponding waveform information (digital waveform data) from the data storing section 30e based on waveform specifying information for ejection drive contained in the ejection driving supply command, produces analog drive signals converted from the digital waveform information read from the data storing section 30e, and supplies the produced drive signals to the piezoelectric element 401 in synchronous signals. The waveform specifying information is identification information and the like attached to signal waveform for ejection drive corresponding to ejection intensity.

The second drive signal supplying section 30f further has function of stopping drive signal supply in response to the ejection stop command received from the operation control section 30a. According to this embodiment, supply of drive signals is stopped after supply of final waveform in one cycle being supplied to the piezoelectric element 401 when stop command is inputted from the operation control section 30a during supply of drive signals.

The synchronous signal generating section 30g includes an oscillator such as ceramic oscillator and crystal oscillator, a counter (or PLL circuit) and other components, and produces synchronous signals based on reference clock signals clk outputted from the oscillator. The synchronous signal generating section 30g supplies the reference clock signals and synchronous signals to the drive signal supplying section 30f.

The drive unit 30 has a computer system which provides functions of the respective sections described above by software and executes the software for controlling hardware necessary for providing the functions. Though not shown in the figure, the hardware structure of this computer system includes a processor, a RAM (random access memory), and a ROM (read only memory) connected with one another via various internal and external buses.

Furthermore, display device such as CRT and LCD monitor, and input device such as operation panel, mouse, and keyboard are connected with the buses via input/output interface (I/F) such as IEEE1394, USB, and parallel port.

When power is supplied, various computer programs dedicated for providing the functions of the respective sections and stored in the ROM in advance are loaded into the RAM under the control of the system program stored in the ROM or the like. Then, predetermined controls and calculations are performed by the processor using various resources according to commands written in the programs loaded to the RAM to provide the respective functions.

The attachment structure of the piezoelectric element 50 and the distortion gauge 51 to the connection flow path pipe 200 is now discussed with reference to FIGS. 6 and 7A through 7D.

Figure 6:
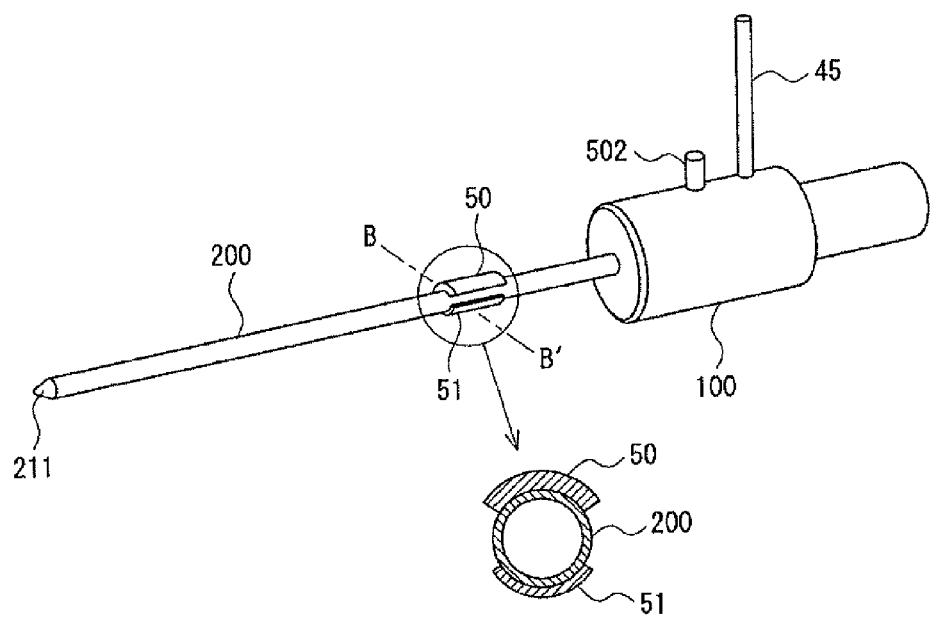
FIG. 6 illustrates an attachment structure of a piezoelectric element and a distortion gauge to a connection flow path pipe.

FIG. 6 illustrates the attachment structure of the piezoelectric element 50 and the distortion gauge 51 to the connection flow path pipe 200. FIGS. 7A through 7D illustrate other examples of the attachment structure of the piezoelectric element 50 and the distortion gauge 51 to the connection flow path pipe 200.

As illustrated in FIG. 6, the piezoelectric element 50 and the distortion gauge 51 are disposed and fixed to the outer circumferential surface of the connection flow path pipe 200 at positions closer to the pulse generating unit 100.

As can be seen from a cross-sectional view positioned in the lower part of FIG. 6 and taken along a line B-B' in a circled portion in the upper part of FIG. 6, the piezoelectric element 50 and the distortion gauge in this embodiment are fixed to the outer circumferential surface (curved surface) of the connection flow path pipe 200 having annular cross section.

Thus, attachment portions of the piezoelectric element 50 and the distortion gauge 51 are so bended as to be closely fixed to the curved outer circumferential surface of the connection flow path pipe 200.

Figure 7A:
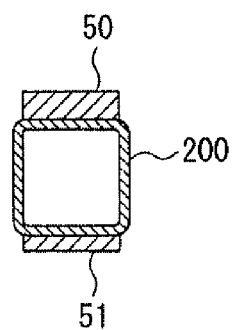
FIGS. 7A through 7D show other examples of the attachment structure of the piezoelectric element and the distortion gauge to the connection flow path pipe.

The attachment structure of the piezoelectric element 50 and the distortion gauge 51 is not limited to this structure, but may be a structure shown in FIG. 7A, for example. According to this structure, at least the attachment portion of the connection flow path pipe 200 to which the piezoelectric element 50 and the distortion gauge 51 are attached is formed in such a shape as to have a rectangular cross section and thus have a horizontal surface on the outer circumferential surface. Then, the piezoelectric element 50 and the distortion gauge 51 are disposed and fixed to the horizontal surface thus formed.

Figure 7B:
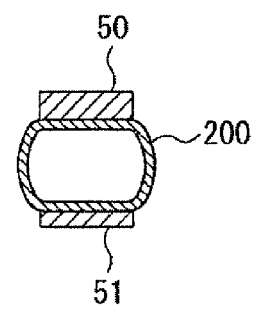
Figure 7C:
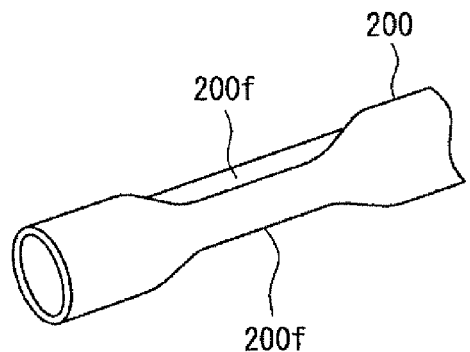

Alternatively, as illustrated in FIGS. 7B and 7C, the piezoelectric element 50 and the distortion gauge may be disposed and fixed to a horizontal surface formed only on the portion of the connection flow path pipe 200 for attachment with the piezoelectric element 50 and the distortion gauge 51 as the surface produced by pressing and crushing the curved surface of the attachment portion having annular cross section or by other method.

Figure 7D:
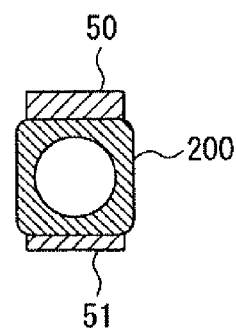

Alternatively, as illustrated in FIG. 7D, the piezoelectric element 50 and the distortion gauge 51 may be disposed and fixed to a horizontal surface corresponding to the portion of the connection flow path pipe 200 for attachment with the piezoelectric element 50 and the distortion gauge 51 as a surface formed on the outer peripheral surface of the outer pipe wall portion having rectangular cross section with the inner hollow portion of the connection flow path pipe 200 having circular cross section.

According to the attachment structures shown in FIGS. 7A through 7D, the necessity for bending the piezoelectric element 50 and the distortion gauge 51 is eliminated by forming the horizontal surface on the outer peripheral surface of the pipe and fixing the piezoelectric element 50 and the distortion gauge 51 to the horizontal surface. Thus, attachment of the piezoelectric element 50 and the distortion gauge 51 can be easily achieved. These attachment structures are effective particularly for piezoelectric element of a type difficult to be bended.

The flow of operation control process for controlling the first drive signal supplying section 30b and the second drive signal supplying section 30f performed by the operation control section 30a is now discussed with reference to FIG. 8.

Figure 8:
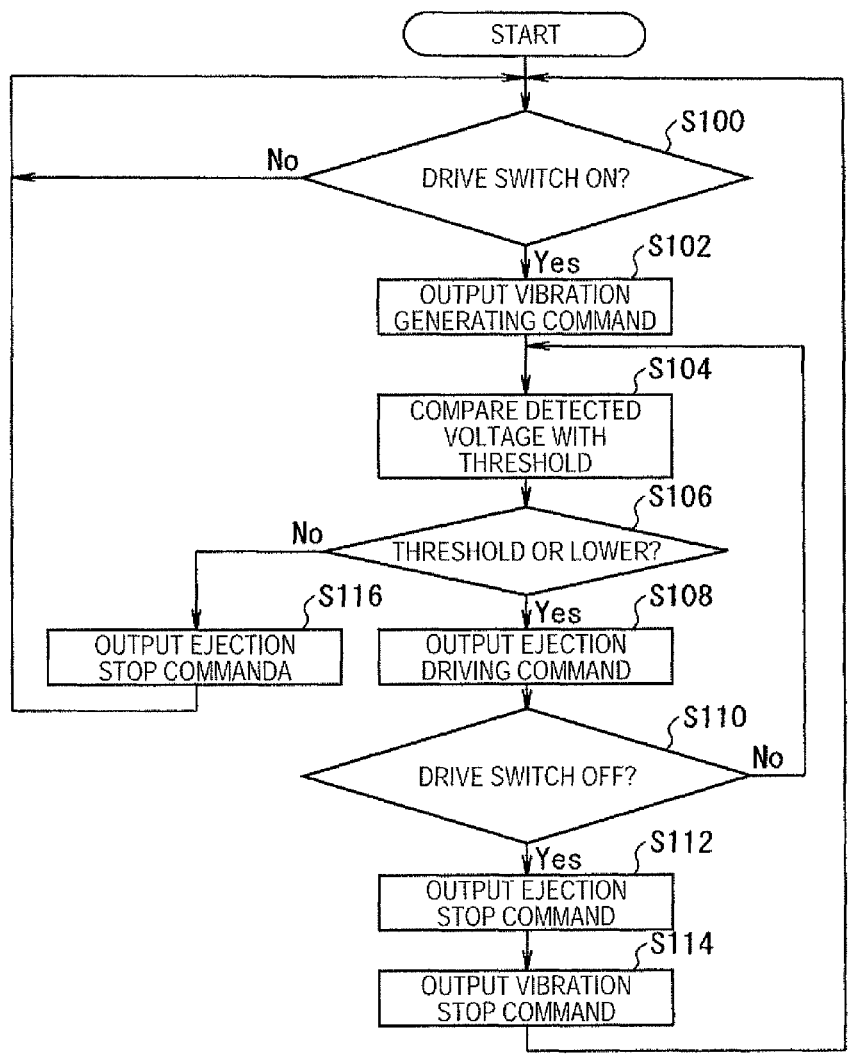
FIG. 8 is a flowchart showing operation control process for controlling a first drive signal supplying section and a second drive signal supplying section performed by an operation control section.

FIG. 8 is a flowchart showing the operation control process for controlling the first drive signal supplying section 30b and the second drive signal supplying section 30f performed by the operation control section 30a.

When the operation control process is initiated under the dedicated program executed by the processor, the flow goes to step S100 as shown in FIG. 8.

In step S100, the operation control section 30a determines whether the drive switch of the water pulse scalpel (hereinafter abbreviated as WPS) is turned on. When it is determined that the drive switch is ON (YES), the flow goes to step S102. When it is determined that the drive switch is not ON (NO), the process is repeated until the drive switch is turned on.

When the flow goes to step S102, the operation control section 30a outputs vibration generating command to the first drive signal supplying section 30b. Then, the flow goes to step S104.

In step S104, the operation control section 30a compares the detected voltage received from the vibration detecting section 30c and the threshold for contact detection stored in the data storing section 30e. Then, the flow goes to step S106.

The comparison in this step may be comparison between the threshold and the detected voltage (absolute value), comparison between the threshold and the average value of the detected voltages (absolute values) for a predetermined period, or other comparison.

According to this embodiment, the average voltage is calculated as in the latter method, and the calculated average is compared with a threshold indicating the average of voltages measured in advance when vibration is weakened by contact between the nozzle 211 and the affected portion, the object in the vicinity of the affected portion or the like.

In step S106, the operation control section 30a determines whether the average of the detected voltages for the predetermined period is equal to or lower than the threshold or not based on the comparison result in step S104. When it is determined that the average is the threshold or lower (YES), the flow goes to step S108. When it is determined that the average is not the threshold or lower (NO), the flow goes to step S116.

When the flow goes to step S108, the operation control section 30a determines that the nozzle 211 contacts the affected portion or the object in the vicinity of the affected portion and outputs ejection driving command to the second drive signal supplying section 30f. Then, the flow goes tot step S110.

In step S110, the operation control section 30a determines whether the drive switch is turned off. When it is determined that the drive switch is off (YES), the flow goes to step S112. When it is determined that the drive switch is not off (NO), the flow goes to step S104.

When the flow goes to step S112, the operation control section 30a outputs ejection stop command to the second drive signal supplying section 30f. Then, the flow goes to step S114.

When the flow goes to step S114, the operation control section 30a outputs vibration stop command to the first drive signal supplying section 30b. Then, the flow goes to step S104.

When the flow goes to step S116 by determination that the nozzle 211 is not under contact condition based on the average of the detected voltages for the predetermined period higher than the threshold, the operation control section 30a outputs ejection stop command to the second drive signal supplying section 30f. Then, the flow goes to step S100. When ejection is not under operation, the flow may go to step S100 without outputting ejection stop command.

The flow of process for supplying drive signals to the piezoelectric element 50 performed by the first drive signal supplying section 30b is now discussed with reference to FIG. 9.

Figure 9:
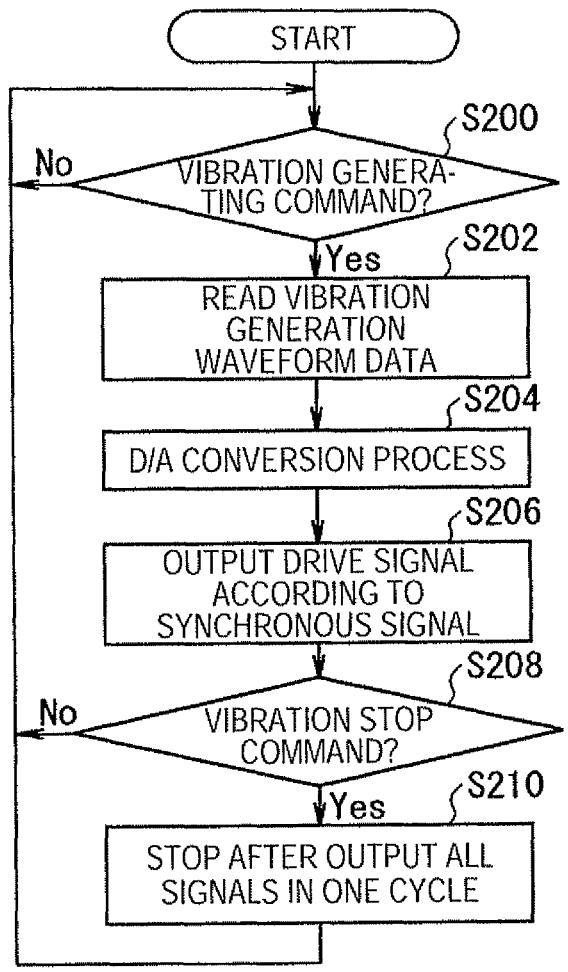
FIG. 9 is a flowchart showing drive signal supply process performed by the first drive signal supplying section.

FIG. 9 is a flowchart showing the drive signal supply process performed by the first drive signal supplying section 30b.

When the process for supplying drive signals to the piezoelectric element 50 is initiated under the dedicated program executed by the processor, the flow goes to step S200 as shown in FIG. 9.

In step S200, the first drive signal supplying section 30b determines whether vibration generating command is inputted from the operation control section 30a. When it is determined that the vibration generating command is inputted (YES), the flow goes to step S202. When it is determined that the vibration generating command is not inputted (NO), the determining process is repeated until the command is inputted.

When the flow goes to step S202, the first drive signal supplying section 30b reads vibration generation waveform data used for driving the piezoelectric element from the data storing section 30e based on the identification information of the specified waveform contained in the vibration generating command. Then, the flow goes to step S204.

In step S204, the first drive signal supplying section 30b converts the digital waveform signals of the waveform data read in step S202 into analog waveform signals. Then, the flow goes to step S206.

In step S206, the first drive signal supplying section 30b outputs drive signals having the analog signal waveform obtained by D/A conversion in step S204 to the piezoelectric element 50 in synchronization with synchronous signals from the synchronous signal generating section 30g. Then, the flow goes to step S208.

In step S208, the first drive signal supplying section 30b determines whether vibration stop command is inputted from the operation control section 30a. When it is determined that the vibration stop command is inputted (YES), the flow goes to step S210. When it is determined that the vibration stop command is not inputted (NO), the drive signal output process in step S204 is continued.

When the flow goes to step S210, the first drive signal supplying section 30b stops drive signal supply after output of all signals in one cycle. Then, the flow goes to step S200.

The flow of process for supplying drive signals to the piezoelectric element 401 performed by the second drive signal supplying section 30f is now discussed with reference to FIG. 10.

Figure 10:
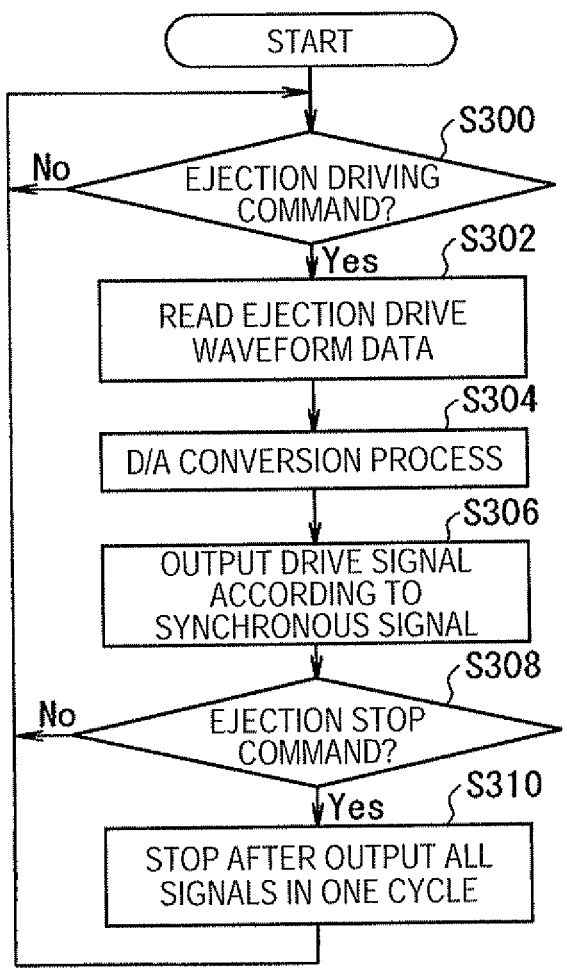
FIG. 10 is a flowchart showing drive signal supply process performed by the second drive signal supplying section.

FIG. 10 is a flowchart showing the drive signal supply process performed by the second drive signal supplying section 30f.

When the process for supplying drive signals to the piezoelectric element 401 is initiated under the dedicated program executed by the processor, the flow goes to step S300 as shown in FIG. 10.

In step S300, the second drive signal supplying section 30f determines whether ejection driving command is inputted to the operation control section 30a. When it is determined that the ejection driving command is inputted (YES), the flow goes to step S302. When it is determined that the ejection driving command is not inputted (NO), the determining process is repeated until the command is inputted.

When the flow goes to step S302, the second drive signal supplying section 30f reads ejection drive waveform data used for driving the piezoelectric element 401 from the data storing section 30e based on the identification information of the specified waveform contained in the ejection driving command. Then, the flow goes to step S304.

In step S304, the second drive signal supplying section 30f converts digital waveform signals having the waveform data read in step S302 into analog waveform signals. Then, the flow goes to step S306.

In step S306, the second drive signal supplying section 30f outputs drive signals having the analog signal waveform obtained by D/A conversion in step S304 to the piezoelectric element 401 in synchronization with synchronous signals from the synchronous signal generating section 30g. Then, the flow goes to step S308.

In step S308, the second drive signal supplying section 30f determines whether the ejection stop command is inputted from the operation control section 30a. When it is determined that the ejection stop command is inputted (YES), the flow goes to step S310. When it is determined that the ejection stop command is not been inputted (NO), the drive signal output process in step S304 is continued.

When the flow goes to step S310, the second drive signal supplying section 30f stops drive signal supply after output of all signals in one cycle. Then, the flow goes to step S300.

The specific operation of the fluid ejection device 1 in this embodiment is herein described with reference to FIG. 11.

Figure 11:
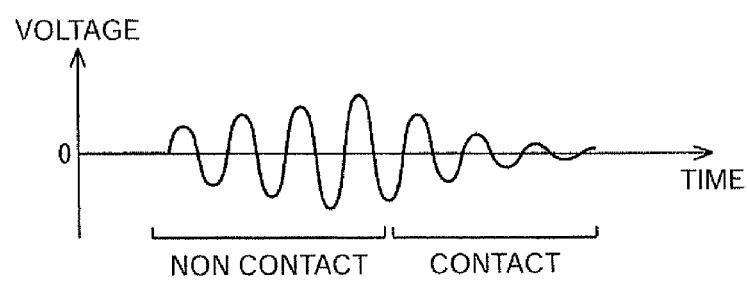
FIG. 11 shows an example of vibration waveform of a nozzle during contact and non-contact.

FIG. 11 shows an example of vibration waveform during contact and non contact of the nozzle 211.

When the power source of the fluid ejection device 1 is turned on, initialization operation is performed. Then, the process proceeds to drive standby condition.

When the drive switch of the WPS is turned on under this condition ("YES" branch in step S100), the operation control section 30a outputs vibration generating command to the first drive signal supplying section 30b (step S102).

When receiving the vibration generating command from the operation control section 30a ("YES" branch in step S200), the first drive signal supplying section 30b reads vibration generation waveform data from the data storing section 30e and supplies the vibration generation waveform data to the work memory such as RAM. Then, the first drive signal supplying section 30b converts the read digital waveform data into analog waveform signals (step S204).

Subsequently, the first drive signal supplying section 30b outputs the analog vibration generation waveform signals thus produced to the piezoelectric element 50 in synchronization with synchronous signals from the synchronous signal generating section 30g (step S206).

By this step, the piezoelectric element 50 expands and contracts to produce expanding and contracting force (vibrating force). This vibrating force is transmitted to the connection flow path pipe 200 via the attachment portion to bend the connection flow path pipe 200 in the direction of applying the force thereto. The connection flow path pipe 200 and the nozzle 211 vibrate by the bending force and restoring force from the bended condition. In this case, larger vibration can be generated from smaller force by driving the piezoelectric element 50 such that the applied vibrating force has the natural frequency of the connection flow path pipe 200.

The deformation of the connection flow path pipe 200 caused by the vibration transmits distortion to an inside resistor (line and foil) through a base (attachment portion) of the distortion gauge 51. The vibration detecting section 30c detects resistance change corresponding to the produced distortion in the detection circuit as voltage, and outputs the detected voltage to the operation control section 30a.

Under non-contact condition of the nozzle 211 with the affected portion, the object in the vicinity of the affected portion or the like, the vibration produced on the nozzle 211 has an amplitude shown in the left part of FIG. 11 larger than the amplitude of the waveform at the time of contact of the nozzle 211 shown in the right part of FIG. 11 at the vibration detecting section 30c.

This is because vibration is weakened by the contact between the nozzle 211 and the affected portion, the object in the vicinity of the affected portion or the like.

The operation control section 30a calculates the average of the absolute values of the detected voltages for the predetermined period, and compares the average with the threshold stored in the data storing section 30e (step S104).

Then, the operation control section 30a outputs ejection driving command to the second drive signal supplying section 30f based on the comparison determination that the nozzle 211 contacts the affected portion or the object in the vicinity of the affected portion when the average is the threshold or lower ("YES" branch in step S106) (step S108).

When the average is higher than the threshold ("NO" branch in step S106), the operation control section 30a does not output the ejection driving command to the second drive signal supplying section 30f based on the determination that the nozzle 211 does not contact the affected portion or the object in the vicinity of the affected portion even under the ON condition of the drive switch (step S116).

When receiving the ejection driving command from the operation control section 30a ("YES" branch in step S300), the second drive signal supplying section 30f reads the corresponding ejection drive waveform data from the data storing section 30e based on the identification information of the waveform information contained in the ejection driving command, and supplies the ejection drive waveform data to the work memory such as RAM (step S302).

Then, the digital waveform data supplied to the work memory is converted to analog data to produce analog drive signals (step S304).

Subsequently, the second drive signal supplying section 30f outputs the analog drive signals for ejection drive thus produced to the piezoelectric element 401 in synchronization with the synchronous signal generating section 30g (step S306).

In this case, fluid is kept supplied to the inlet flow path 503 with constant liquid pressure by using the pump 20 before drive signals are supplied. Thus, fluid flows into the fluid chamber 501 by the difference between the delivering force of the pump 20 and the fluid resistance of the entire inlet flow path when the piezoelectric element 401 does not operate.

When the piezoelectric element 401 rapidly expands in response to a drive signal inputted to the piezoelectric element 401, the pressure inside the fluid chamber 501 rapidly increases to several tens of atms. under the condition of sufficient inertances L1 and L2 on the inlet flow path side and the outlet flow path side.

This pressure is considerably higher than the pressure applied to the inlet flow path 503 by the pump 20. Thus, the flow amount of the fluid from the inlet flow path side into the fluid chamber 501 decreases, and the flow amount of the fluid discharged from the outlet flow path 511 increases due to the high pressure.

However, the inertance L1 of the inlet flow path 503 is larger than the inertance L2 of the outlet flow path 511. In this case, the increase amount of the fluid discharged from the outlet flow path becomes larger than the decrease amount of the fluid flowing from the inlet flow path 503 into the fluid chamber 501. Thus, pulsed fluid delivery, that is, pulsed flow is produced in the connection flow path 201. The pressure change at the time of delivery is transmitted through the connection flow path pipe 200, and fluid is ejected from the fluid ejection opening 212 at the end of the nozzle 211.

The diameter of the fluid ejection opening 212 of the nozzle 211 is smaller than that of the outlet flow path 511. Thus, fluid is ejected as high-speed pulsed liquid drops.

The inside of the fluid chamber 501 is brought into vacuum condition immediately after pressure increase by interaction of the decrease in the fluid flow-in amount from the inlet flow path 503 and the increase in the fluid discharge amount from the outlet flow path 511.

Then, the expanded piezoelectric element 401 comes to contract at a speed corresponding to the falling shape of the drive waveform, and the flow of fluid finally returns to the steady condition before supply of the drive signals.

In this structure, the fluid chamber 501 has a substantially rotational body and the inlet flow path 503, and the outlet flow path 511 is formed in the vicinity of the rotation axis of the substantially rotational body of the fluid chamber 501. Thus, rotational flow is generated within the fluid chamber 501, and bubbles (vacuum bubbles and gas bubbles) contained in the fluid are rapidly discharged from the outlet flow path 511 to the outside.

The pulsed flow can be continuously ejected from the nozzle 211 by successively supplying drive signals to the piezoelectric element 401.

When the operator moves the pulse generating unit 100 and separates the nozzle 211 from the affected portion or the object in the vicinity of the affected portion under the condition in which pulsed flow is continuously ejected in response to successive supply of drive signals, thereby removing any factor for preventing vibration of the nozzle 211, the voltage detected by the vibration detecting section 30c increases.

By this step, the average of the absolute values of the detected voltages for the predetermined period becomes higher than the threshold ("NO" branch in step S106). Then, the operation control section 30a outputs ejection stop command to the second drive signal supplying section 30f based on determination that the nozzle 211 does not contact the affected portion or the object in the vicinity of the affected object (step S116).

When receiving the ejection stop command from the operation control section 30a ("YES" branch in step S308), the second drive signal supplying section 30f stops drive signal supply after supply of all drive signals currently supplied in one cycle (step S310).

When the nozzle 211 again contacts the affected portion or the object in the vicinity of the affected portion under the ON condition of the drive switch of the WPS, the vibration of the nozzle 211 is weakened. As a result, the voltage detected by the vibration detecting section 30c decreases.

By this step, the average of the absolute values of the detected voltages for the predetermined period becomes the threshold or lower ("YES" branch in step S106). Then, the operation control section 30a outputs ejection driving command to the second drive signal supplying section 30f based on determination that the nozzle 211 contacts the affected portion or the object in the vicinity of the affected portion (step S108). By this step, drive signals are supplied to the piezoelectric element 401, and ejection of pulsed flow is restarted.

When the drive switch of the WPS is turned off by the operator under this condition, the operation control section 30a determines that the drive switch has been turned off ("YES" branch in step S110). Then, the operation control section 30a outputs ejection stop command to the second drive signal supplying section 30f (step S112).

By this step, the second drive signal supplying section 30f stops drive signal supply after supplying of all drive signals currently supplied in one cycle (step S310). By suspension of drive signal supply, ejection of the pulsed flow stops accordingly.

Then, the operation control section 30a outputs vibration stop command to the first drive signal supplying section 30b (step S114).

By this step, the first drive signal supplying section 30b stops drive signal supply after supply of all drive signals currently supplied in one cycle (step S210). By suspension of drive signal supply, vibration stops accordingly.

According to the fluid ejection device 1 in this embodiment, the first drive signal supplying section 30b drives the vibration generating piezoelectric element 50 to vibrate the nozzle 211 when the drive switch of the WPS is ON. Moreover, the vibration detecting section 30c detects the level of the vibration, and the operation control section 30a determines whether the nozzle 211 contacts the affected portion or the like based on the detection result. When it is determined that the nozzle 211 contacts the affected portion or the like, the operation control section 30a outputs ejection driving command to the second drive signal supplying section 30f. The second drive signal supplying section 30f supplies drive signals to the capacity changing piezoelectric element 401 in response to ejection driving command to change the capacity of the fluid chamber 501 and perform ejection of fluid.

When it is determined that the nozzle 211 does not contact the affected portion or the like, the operation control section 30a outputs ejection stop command to the second drive signal supplying section 30f.

The second drive signal supplying section 30f stops drive signal supply to the capacity changing piezoelectric element 401 in response to the ejection stop command to stop ejection of fluid.

The operation control section 30a does not output ejection driving command to the second drive signal supplying section 30f while ejection of fluid is not performed under the ON condition of the drive switch of the WBS.

By this method, ejection is suspended when the nozzle 211 does not contact the affected portion or the like. Thus, ejection of pulsed flow in an unexpected direction (such as direction toward eyes of a doctor or a nurse in the operation room and a portion not desired to be removed) and scattering of tissue pieces cut by the ejection in an unexpected direction or position can be prevented when the nozzle 211 is separated from the affected portion or the object in the vicinity of the affected portion (such as liquid reservoir of ejected fluid or blood) by operation error of the operator (doctor in charge).

According to the first embodiment, the nozzle 211 and the fluid ejection opening 212 correspond to a fluid ejection opening as referred to in any of the first, second, fourth and fourteenth aspects. The capacity changing section 405 and the second drive signal supplying section 30f correspond to a capacity changing unit as referred to in any of the first, thirteenth and fourteenth aspects. The fluid container 10 and the pump 20 correspond to a fluid supplying unit as referred to in any of the first and fourteenth aspects. The piezoelectric element 50 and the first drive signal supplying section 30b correspond to a vibrating unit as referred to in any of the first, fourth and fourteenth aspects. The distortion gauge 51 and the vibration detecting section 30c correspond to a vibration detecting unit as referred to in any of the first, fourth, thirteenth and fourteenth aspects. The operation control section 30a corresponds to an operation control unit as referred to in any of the first, thirteenth and fourteenth aspects. The piezoelectric element 50 corresponds to a vibrating force generating section as referred to in any of the fourth, fifth and ninth aspects. The distortion gauge 51 corresponds to a vibration receiving section as referred to in any of the fourth, fifth and eighth aspects.

Second Embodiment

Figure 12:
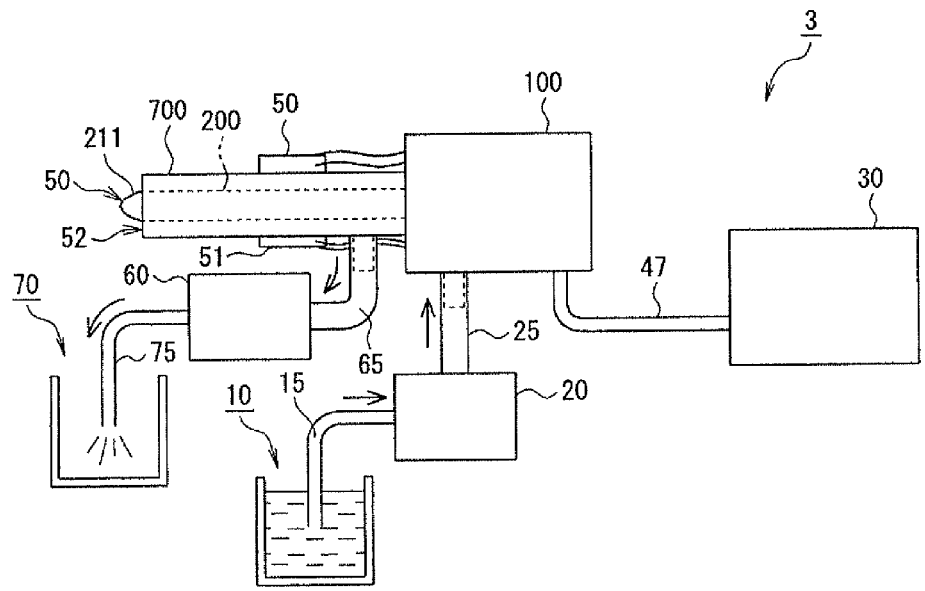
FIG. 12 illustrates a general structure of a fluid ejection device according to a second embodiment.
Figure 13:
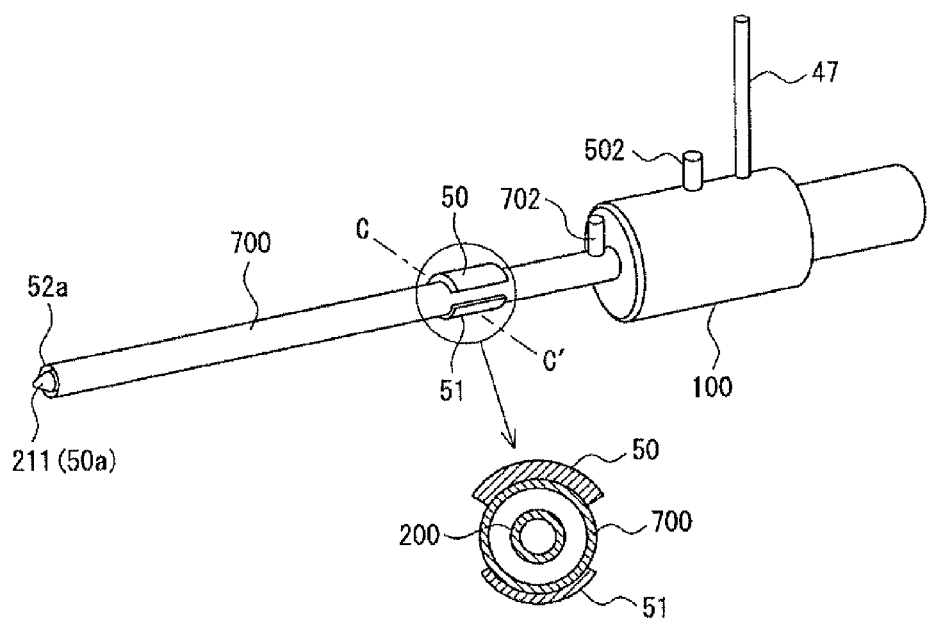
FIG. 13 illustrates an attachment structure of the piezoelectric element and the distortion gauge to a suction pipe.

A second embodiment according to an aspect of the invention is hereinafter described. FIGS. 12 through 14 show a fluid ejection device, a driving method of a fluid ejection device, and an operating instrument according to the second embodiment of an aspect of the invention.

The second embodiment is different from the first embodiment in that components such as a suction pipe and a pump disposed in such positions as to cover the connection flow path pipe 200 are equipped to suck an object close to the nozzle 211 and give sucking force, respectively, and that the vibration generating piezoelectric element 50 and the distortion gauge 51 are provided on the outer circumferential surface of the suction pipe. Other parts are similar to those of the first embodiment. In the following description, only the different parts are discussed in detail. Similar reference numerals are given to similar parts, and explanation of the similar parts is not repeated.

The structure of the fluid ejection device according to this embodiment is now described with reference to FIG. 12. FIG. 12 illustrates a general structure of a fluid ejection device 3 according to this embodiment.

As illustrated in FIG. 12, the fluid ejection device 3 has a basic structure including the fluid container 10 for storing fluid, the pump 20 as a pressure generating unit, a suction container 70 for storing sucked object, a suction pump 60 as sucking force giving unit, the pulse generating unit 100 for generating pulsed flow of fluid supplied from the pump 20, the drive unit for driving the pulse generating unit 100, the vibration generating piezoelectric element 50, and the distortion gauge 51.

The pulse generating unit 100 is connected with the connection fluid path pipe 200 having narrow pipe shape. The nozzle 211 having a diameter smaller than the flow path diameter of the connection flow path pipe 200 is inserted into the end of the connection flow path pipe 200.

A pipe-shaped suction pipe 700 having a diameter larger than that of the connection flow path pipe 200 and containing the connection flow path pipe 200 is connected with the pulse generating unit 100.

A passage through which sucked object such as delivered liquid and tissue pieces passes is formed between the inner circumferential surface of the suction pipe 700 and an outer circumferential surface of the connection flow path pipe 200 having a different diameter from that of the suction pipe 700.

An outlet flow path pipe 702 through which the sucked object is supplied to the suction container 70 projects from the suction pipe 700 on the pulse generating unit 100 side. The sucked object is attracted by the suction pump 60 via a connection tube 65 connected with the outlet flow path pipe 702, and discharged toward the suction container 70 via a connection tube 75.

Passages along which two supply lines VPZT(−) and VPZT(+) for supplying drive signals to the piezoelectric element 50, gauge input line and gauge output line for the distortion gauge 51, and two supply lines JPZT(−) and JPZT(+) for supplying drive signals to the fluid ejecting piezoelectric element 401 (described later) are wired are formed inside the pulse generating unit 100.

These passages are joined at the exit of the signal lines extending from the pulse generating unit 100, and the four supply lines and the gauge input line and gauge output line collected at one position of the exit extend to the outside.

These lines are collected by a cable 47 and connected with the drive unit 30. The respective lines of the cable 47 are electrically connected with the corresponding components of the drive unit 30.

The attachment structure of the piezoelectric element 50 and the distortion gauge 51 to the suction pipe 700 is now explained with reference to FIG. 13 and FIGS. 14A through 14D.

FIG. 13 illustrates the attachment structure of the piezoelectric element 50 and the distortion gauge 51 to the suction pipe 700. FIGS. 14A through 14D show other examples of the attachment structure of the piezoelectric element 50 and the distortion gauge 51 to the suction pipe 700.

As illustrated in FIG. 13, the piezoelectric element 50 and the distortion gauge 51 in this embodiment are disposed and fixed to the outer circumferential surface of the suction pipe 700 at positions closer to the pulse generating unit 100.

Also, the piezoelectric element 50 and the distortion gauge 51 are fixed to the circumferential surface (curved surface) having annular cross section as shown in a cross-sectional view positioned in the lower part of FIG. 13 corresponding to a portion circled and taken along a line C-C' in the upper part of FIG. 13.

Thus, attachment portions of the piezoelectric element 50 and the distortion gauge 51 are so banded as to be closely fixed to the curved outer circumferential surface of the suction pipe 700.

Figure 14A:
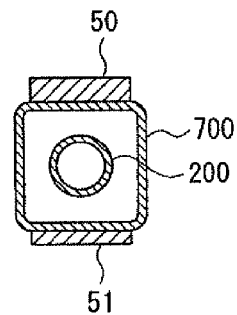
FIGS. 14A through 14D show other examples of the attachment structure of the piezoelectric element and the distortion gauge to the suction pipe.

The attachment structure of the piezoelectric element 50 and the distortion gauge 51 is not limited to this structure, but may be a structure shown in FIG. 14A, for example. According to this structure, at least the attachment portion of the suction pipe 700 to which the piezoelectric element 50 and the distortion gauge 51 are attached is formed in such a shape as to have a rectangular cross section and thus have a horizontal surface on the outer circumferential surface. Then, the piezoelectric element 50 and the distortion gauge 51 are disposed and fixed to the horizontal surface thus formed.

Figure 14B:
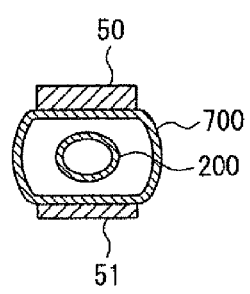
Figure 14C:
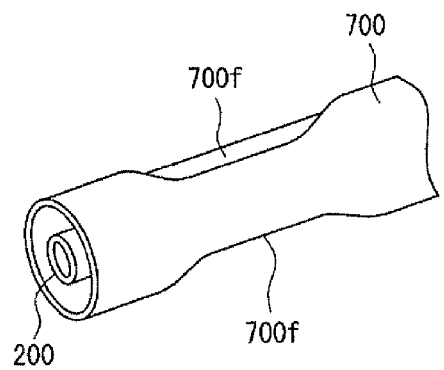

Alternatively, as illustrated in FIGS. 14B and 14C, the piezoelectric element 50 and the distortion gauge 51 may be disposed and fixed to a horizontal surface formed only on the portion of the suction pipe 700 for attachment with the piezoelectric element 50 and the distortion gauge 51 as the surface produced by pressing and crushing the curved surface of the attachment portion having annular cross section or by other method.

Figure 14D:
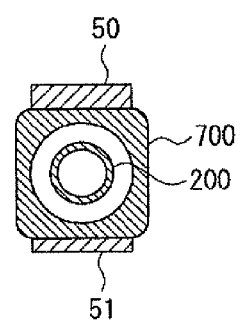

Alternatively, as illustrated in FIG. 14D, the piezoelectric element 50 and the distortion gauge 51 may be disposed and fixed to a horizontal surface corresponding to the portion for attachment with the piezoelectric element 50 and the distortion gauge 51 as a surface formed on the outer peripheral surface of the outer pipe wall portion having rectangular cross section with the inner hollow portion of the suction pipe 700 having circular cross section.

According to the attachment structures shown in FIGS. 14A through 14D, the necessity for bending the piezoelectric element 50 and the distortion gauge 51 is eliminated by forming the horizontal surface on the outer peripheral surface of the pipe and fixing the piezoelectric element 50 and the distortion gauge 51 to the horizontal surface. Thus, attachment of the piezoelectric element 50 and the distortion gauge 51 can be easily achieved. These attachment structures are effective particularly for piezoelectric element of a type difficult to be bended.

When the piezoelectric element 50 expands and contracts in response to drive signals for vibration generation supplied from the first drive signal supplying section 30b in this structure, this expanding and contracting force (vibrating force) is transmitted to the suction pipe 700 via the attachment portion to bend the suction pipe 700 in the direction of applying the force thereto. The suction pipe 700 vibrates by the bending force and restoring force from the bended condition. In this case, larger vibration can be generated from smaller force by driving the piezoelectric element 50 such that the applied vibrating force has the natural frequency of the suction pipe 700.

The deformation of the suction pipe 700 caused by the vibration transmits distortion to an inside resistor (line and foil) through a base (attachment portion) of the distortion gauge 51. The vibration detecting section 30c detects resistance change corresponding to the produced distortion in the detection circuit as detected voltage, and outputs the detected voltage to the operation control section 30a.

Under non-contact condition of the end of the suction pipe 700 with the affected portion, the object in the vicinity of the affected portion or the like, the vibration produced on the suction pipe 700 has an amplitude shown in the left part of FIG. 11 larger than the amplitude of the waveform at the time of contact of the suction pipe 700 shown in the right part of FIG. 11 at the vibration detecting section 30c similarly to the first embodiment.

This is because vibration is weakened by the contact between the end of the suction pipe 700 such as the opening and the affected portion, the object in the vicinity of the affected portion or the like.

When the drive switch of the WPS is turned on with the end of the suction pipe 700 contacting with the affected portion, the object in the vicinity of the affected portion or the like, the average of the absolute values of the detected voltages becomes the threshold or lower. Thus, the operation control section 30a detects contact condition, and outputs ejection driving command to the second drive signal supplying section 30f.

By this step, the piezoelectric element 401 of the capacity changing section 405 operates to eject high-pressure fluid (pulsed flow).

When the end of the suction pipe 700 is separated from the affected portion or the object in the vicinity of the affected portion, the average of the absolute values of the detected voltages becomes larger than the threshold. Thus, the operation control section 30a detects non-contact condition and does not output ejection driving command to the second signal supplying section 30f even in the ON condition of the drive switch.

While ejection is being performed under this condition, the operation control section 30a outputs ejection stop command to the second drive signal supplying section 30f. By this step, driving of the piezoelectric element 401 of the capacity changing unit 405 stops, and ejection of fluid (pulsed flow) stops accordingly.

The operation of the drive unit 30 is similar to that of the first embodiment except that the target to be vibrated is not the nozzle 211 and the connection flow pipe 200 but the suction pipe 700.

According to the fluid ejection device 3 in this embodiment, the first drive signal supplying section 30b drives the vibration generating piezoelectric element 50 to vibrate the suction pipe 700 when the drive switch of the WPS is ON. Also, the vibration detecting section 30c detects the level of the vibration, and the operation control section 30a determines whether the opening or other end portion of the suction pipe 700 contacts the affected portion or the like based on the detection result. When it is determined that the end of the suction pipe 700 contacts the affected portion or the like, the operation control section 30a outputs ejection driving command to the second drive signal supplying section 30f. The second drive signal supplying section 30f supplies drive signals to the capacity changing piezoelectric element 401 in response to ejection driving command to change the capacity of the fluid chamber 501 and perform ejection of fluid.

When it is determined that the end of the suction pipe 700 does not contact the affected portion or the like, the operation control section 30a outputs ejection stop command to the second drive signal supplying section 30f.

The second drive signal supplying section 30f stops drive signal supply to the capacity changing piezoelectric element 401 in response to the ejection stop command to stop ejection of fluid.

The operation control section 30a does not output ejection driving command to the second drive signal supplying section 30f while ejection of fluid is not performed under the ON condition of the drive switch of the WPS.

By this method, ejection operation is suspended when the end of the suction pipe 700 and the nozzle 211 do not contact the affected portion or the like. Thus, ejection of pulsed flow in an unexpected direction (such as direction toward eyes of a doctor or a nurse in the operation room and a portion not desired to be removed) and scattering of tissue pieces cut by the ejection in an unexpected direction or position can be prevented when the nozzle 211 and the end of the suction pipe 700 are separated from the affected portion or the object in the vicinity of the affected portion (such as liquid reservoir of ejected fluid or blood) by operation error of the operator (doctor in charge).

According to the second embodiment, the nozzle 211 and the fluid ejection opening 212 correspond to a fluid ejection opening as referred to in any of the third and fourth aspects. The capacity changing section 405 and the second drive signal supplying section 30f correspond to a capacity changing unit as referred to in any of the third and thirteenth aspects. The fluid container 10 and the pump 20 correspond to a fluid supplying unit as referred to the third aspect. The suction pipe 700 corresponds to a suction pipe as referred to in any of the third, sixth and seventh aspects. The suction pump 60 corresponds to a sucking force giving unit as referred to in the third aspect. The piezoelectric element 50 and the first drive signal supplying section 30b correspond to a vibrating unit as referred to in any of the third and fourth aspects. The distortion gauge 51 and the vibration detecting section 30c correspond to a vibration detecting unit as referred to in any of the third, fourth and thirteenth aspects. The operation control section 30a corresponds to an operation control unit as referred to in any of the third and thirteenth aspects. The piezoelectric element 50 corresponds to a vibrating force generating section as referred to in any of the sixth, seventh and ninth aspects. The distortion gauge 51 corresponds to vibration receiving section as referred to in any of the sixth, seventh and eighth aspects.

Third Embodiment

A third embodiment according to an aspect of the invention is hereinafter described. FIGS. 15A through 17B show a fluid ejection device, a driving method of a fluid ejection device, and an operating instrument according to the third embodiment of an aspect of the invention.

The third embodiment is different from the first and second embodiments in that application of vibrating force to the connection flow path pipe 200 or the suction pipe 700 and detection of the level of vibration are achieved by time divisions using a single piezoelectric element provided on the connection flow path pipe 200 or the suction pipe 700. Thus, a part of the drive unit 30 is different from the drive unit 30 of the first and second embodiments. Other parts are similar to those of the first and second embodiments. In the following description, only the different parts are discussed in detail. Similar reference numerals are given to similar parts, and explanation of the similar parts is not repeated.

The attachment structure of a piezoelectric element 52 having both functions of giving vibrating force and receiving vibration in this embodiment is initially described with reference to FIGS. 15A and 15B.

Figure 15A:
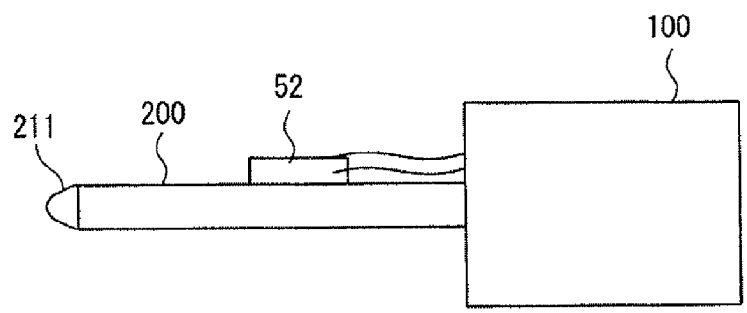
FIG. 15A shows an example of an attachment structure of a piezoelectric element to the connection flow path pipe.

FIG. 15A shows an example of the attachment structure of the piezoelectric element 52 to the connection flow path pipe 200. FIG. 15B shows an example of the attachment structure of the piezoelectric element 52 to the suction pipe 700.

According to this embodiment, application of vibrating force and detection of the level of vibration are achieved by the single piezoelectric element 52. Thus, the distortion gauge 51 employed in the first and second embodiments can be eliminated.

In case of the fluid ejection device 1 having no suction pipe, the single piezoelectric element 52 is disposed and fixed to the outer circumferential surface of the connection flow path pipe 200 at a position shifted toward the nozzle 211 from the outlet flow path pipe 510 similarly to the piezoelectric element 50 in the first embodiment as illustrated in FIG. 15A.

The attachment structure of the piezoelectric element 52 may be any of the attachment structure of the piezoelectric element 50 shown in FIG. 6 and the structures shown in FIGS. 7A through 7B in the first embodiment.

Figure 15B:
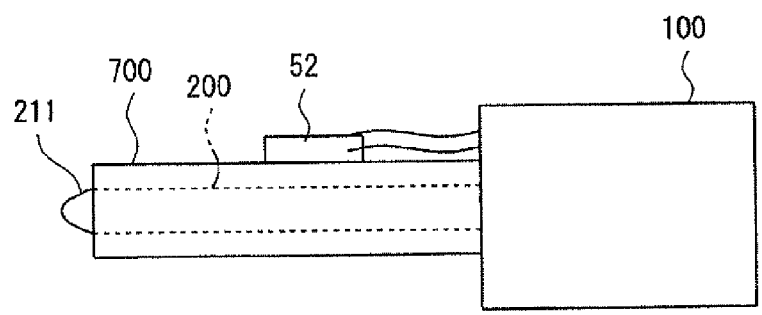
FIG. 15B shows an example of an attachment structure of a piezoelectric element to the suction pipe.

In case of the fluid ejection device 3 having the suction pipe, the single piezoelectric element 52 is disposed and fixed to the outer circumferential surface of the suction pipe 700 at a position closer to the pulse generating unit 100 similarly to the piezoelectric element 50 in the second embodiment as illustrated in FIG. 15B.

The attachment structure of the piezoelectric element 52 may be any of the attachment structure of the piezoelectric element 50 shown in FIG. 13 and the structures shown in FIGS. 14A through 14D in the second embodiment.

The detailed structure of a drive unit 30' of the fluid ejection device 1 or 3 including the single piezoelectric element 52 for giving vibrating force and receiving vibration in this embodiment is now discussed with reference to FIG. 16.

Figure 16:
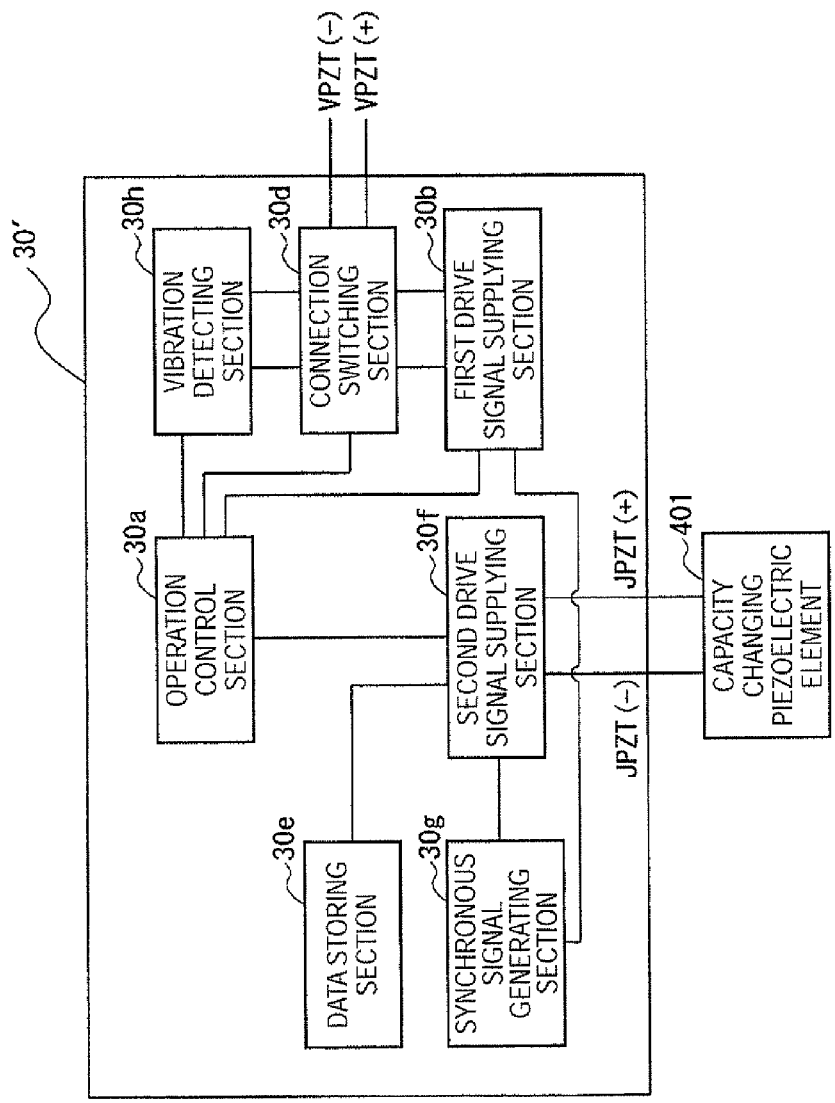
FIG. 16 is a block diagram showing a detailed structure of a drive unit.

FIG. 16 is a block diagram showing the detailed structure of the drive unit 30' according to this embodiment.

As shown in FIG. 16, the drive unit 30' includes the operation control section 30a, the first drive signal supplying section 30b, a vibration detecting unit 30h, a connection switching section 30d, the data storing section 30e, the second drive signal supplying section 30f, and the synchronous signal generating section 30g.

The operation control section 30a has function of issuing operation commands to the respective components in response to operation input received from the input device of the fluid ejection device 1 or 3. More specifically, the operation control section 30a has function of controlling various operation processes such as supplying drive signals from the first drive signal supplying section 30b, switching time divisions performed by the connection switching section 30d, determining contact condition of the nozzle 211 or the end of the suction pipe 700, and supplying drive signals from the second drive signal supplying section 30f based on the determination result.

The connection switching section 30d switches between the electric connection between the supply lines VPZT(−) and VPZT(+) of the piezoelectric element 52 and the vibration detecting section 30h, and the electric connection between the supply lines VPZT(−) and VPZT(+) and the first drive signal supplying section 30b in response to control signals from the operation control section 30a.

The connection may be switched by using a mechanical switch or switching elements such as transistors.

The vibration detecting section 30h detects electromotive force generated on the piezoelectric element 52 by piezoelectric effect caused by vibration of the connection flow path pipe 200 or the suction pipe 700, and outputs the electromotive force to the operation control section 30a as detected voltage.

The operation of the drive unit 30' according to this embodiment is now explained with reference to FIGS. 17A and 17B.

Figures 17A, 17B:
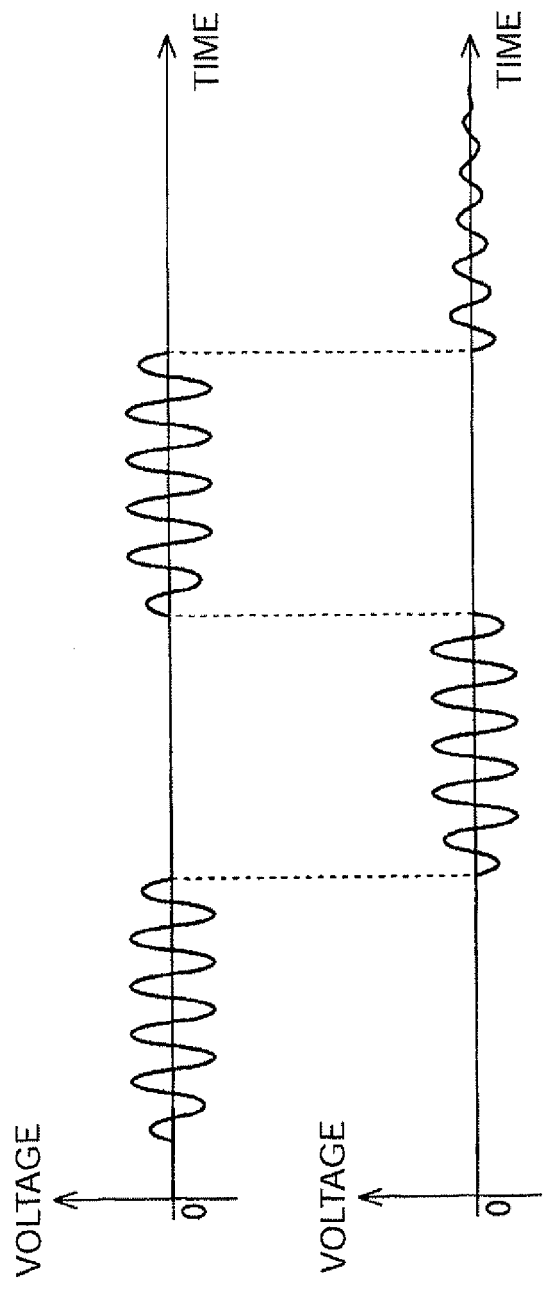
FIG. 17A shows vibration waveform for a period during which vibrating force is applied by the piezoelectric element.
FIG. 17B shows vibration waveform for a period during which vibration is received by the piezoelectric element.

FIG. 17A shows vibration waveform for a period during which vibrating force is given by the piezoelectric element

52. FIG. 17B shows vibration waveform for a period during which vibration is received by the piezoelectric element 52.

The drive unit 30' applies vibrating force and receives vibration generated by the applied vibrating force (conversion from vibration level to voltage by piezoelectric effect in this embodiment) by using the single piezoelectric element 52. When the drive switch of the WPS is turned on, the drive unit 30' controls the operation of the connection switching section 30*d* and the operation of the first drive signal supplying section 30*b* such that the process for supplying drive signals to the piezoelectric element 52 from the first drive signal supplying section 30*b* for a given period and the process for detecting the level of vibration by the vibration detecting section 30*h* for a given period can be alternately repeated by time division.

More specifically, when the drive switch is turned on, the operation control section 30*a* alternately switches between the electric connection between the supply lines VPZT(−) and VPZT(−) of the piezoelectric element 52 and the first drive signal supplying section 30*b* and the electric connection between the supply lines VPZT(−) and VPZT(+) of the piezoelectric element 52 and the vibration detecting section 30*h* by time division by controlling supply contents of control signals given to the connection switching section 30*d*.

Simultaneously, the operation control section 30*a* outputs vibration generating command to the first drive signal supplying section 30*b* at the time of outputting the control signals to the connection switching section 30*d*. By this step, the supply lines VPZT(−) and VPZT (+) of the piezoelectric element 52 are electrically connected with the first drive signal supplying section 30*b*, and the vibration generating command is supplied to the first drive signal supplying section 30*b*.

When receiving the vibration generating command from the operation control section 30*a*, the first drive signal supplying section 30*b* reads vibration generation waveform data from the data storing section 30*e* and supplies the data to the work memory such as RAM. Then, the first drive signal supplying section 30*b* converts the digital waveform data read from the data storing section 30*e* into analog waveform signals.

Subsequently, the first drive signal supplying section 30*b* outputs the drive signals for vibration generation thus generated to the piezoelectric element 52 in synchronization with synchronous signals from the synchronous signal generating section 30*g*.

By this step, the piezoelectric element 52 expands and contracts to produce expanding and contracting force (vibrating force). This vibrating force is transmitted to the connection flow path pipe 200 or the suction pipe 700 via the attachment portion to bend the connection flow path pipe 200 or the suction pipe 700 in the direction of applying the force thereto. The connection flow path pipe 200 or the suction pipe 700 vibrates by the bending force and restoring force from the banded condition. In this case, larger vibration can be generated from smaller force by driving the piezoelectric element 52 such that the applied vibrating force has the natural frequency of the connection flow path pipe 200 or the suction pipe 700.

After elapse of the given period during which the vibrating force is applied, the connection of the connection switching section 30*d* is switched to the connection between the supply lines VPZT(−) and VPZT(+) of the piezoelectric element 52 and the vibration detecting section 30*h* in response to control signals from the operation control section 30*a*. By this step, the given period after switching becomes the detection period by the vibration detecting section 30*h*.

By this method, the vibration generating period and the vibration detecting period are alternately switched for each given period as shown in FIGS. 17A and 17B.

Then, the level of vibration (electromotive force) during detection period in which the nozzle 211 or the end of the suction pipe 700 contacts the affected portion or the like becomes lower than that in the period in which the nozzle 211 or the end of the suction pipe 700 does not contact the affected portion or the like as can be seen from the vibration waveform in the second half of FIG. 17B.

Thus, the vibration detecting section 30*h* detects the electromotive force of the piezoelectric element 52 at this time and compares the detection electromotive force (or average in the corresponding predetermined period) and the threshold to determine whether the vibration has been decreased. By this step, contact between the nozzle 211 or the end of the suction pipe 700 and the affected portion can be detected.

When detecting the contact between the nozzle 211 or the end of the suction pipe 700 and the affected portion, the operation control section 30*a* outputs ejection driving command to the second drive signal supplying section 30*f*.

When non-contact between the nozzle 211 or the end of the suction pipe 700 and the affected portion is detected during ejection, the operation control section 30*a* outputs ejection stop command to the second drive signal supplying section 30*f*.

When the drive switch is turned off, the operation control section 30*a* outputs ejection stop command to the second drive signal supplying section 30*f*. After ejection is stopped, the operation control section 30*a* outputs vibration stop command to the first drive signal supplying section 30*b* and suspends supply of control signals to the connection switching section 30*d*.

Other operations are similar to those in the first embodiment, and thus the same explanation is not repeated.

Accordingly, the fluid ejection device 1 or 3 in this embodiment can perform both application of vibrating force to the connection flow path pipe 200 or the suction pipe 700 and detection of the level of vibration generated by the applied vibrating force by time division by using the single piezoelectric element 52.

Thus, the necessity for providing detection element such as distortion gauge for detecting the level of vibration is eliminated, and the component cost and processing cost associated with the detection element can be reduced.

According to the third embodiment, the nozzle 211 and the fluid ejection opening 212 correspond to a fluid ejection opening as referred to in any of the first, second, third, fourth and fourteenth aspects. The capacity changing section 405 and the second drive signal supplying section 30*f* correspond to a capacity changing unit as referred to in any of the first, second, third, thirteenth and fourteenth aspects. The fluid container 10 and the pump 20 correspond to a fluid supplying unit as referred to in any of the first, second, third, and fourteenth aspects. The suction pipe 700 corresponds to a suction pipe as referred to in any of the third, sixth and seventh aspects. The suction pump 60 corresponds to a sucking force giving unit as referred to in the third aspect. The piezoelectric element 52 and the first drive signal supplying section 30*b* correspond to a vibrating unit as referred to in the eleventh aspect. The piezoelectric element 52 and the vibration detecting section 30*h* correspond to a vibration detecting unit as referred to in the eleventh aspect. The operation control section 30*a* corresponds to an operation control unit as referred to in any of the first, second, third, thirteenth and fourteenth aspects. The operation control section 30*a* and the connection switching section 30*d* correspond to a time division control unit as referred to in the eleventh aspect. The vibration detecting section 30h corresponds to an electromotive force detecting section as referred to in the eleventh aspect. The piezoelectric element 52 corresponds to a vibrating force generating section as referred to in the tenth aspect.

Fourth Embodiment

A fourth embodiment according to an aspect of the invention is hereinafter described. FIGS. 18A through 20 show a fluid ejection device, a driving method of a fluid ejection device, and an operating instrument according to the fourth embodiment of an aspect of the invention.

This embodiment is different from the third embodiment in that larger vibrating force is applied to the connection flow path pipe 200 or the suction pipe 700 by using two piezoelectric elements provided on the connection flow path pipe 200 or the suction pipe 700. Thus, a part of the drive unit is different from the drive unit 30' of the third embodiment. Other parts are similar to those of the third embodiment. In the following description, only the different parts are discussed in detail. Similar reference numerals are given to similar parts, and explanation of the similar parts is not repeated.

The attachment structure of the piezoelectric elements 52 and 53 having functions of both application of vibrating force and detection of vibration in this embodiment is initially described with reference to FIGS. 18A and 18B.

Figure 18A:
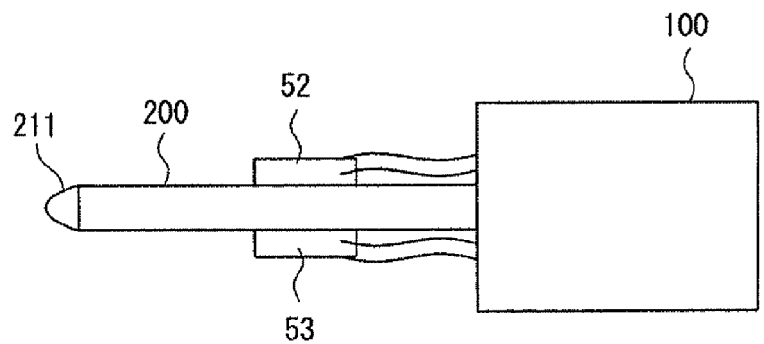
FIG. 18A shows an example of an attachment structure of piezoelectric elements to the connection flow path pipe.

FIG. 18A shows an example of the attachment structure of the piezoelectric elements 52 and 53 to the connection flow path pipe 200. FIG. 18B shows an example of the attachment structure of the piezoelectric elements 52 and 53 to the suction pipe 700.

According to this embodiment, application of vibrating force and detection of the level of vibration are achieved by the two piezoelectric elements 52 and 53.

In case of the fluid ejection device 1 having no suction pipe, the two piezoelectric elements 52 and 53 are disposed and fixed to the outer circumferential surface of the connection flow path pipe 200 at positions shifted toward the nozzle 211 from the outlet flow path pipe 510 and opposed to each other with the pipe interposed therebetween similarly to the piezoelectric element 50 and the distortion gauge 51 in the first embodiment as illustrated in FIG. 18A.

The attachment structure of the piezoelectric elements 52 and 53 may be any of the attachment structure of the piezoelectric element 50 and the distortion gauge 51 shown in FIG. 6 and the structures shown in FIGS. 7A through 7D in the first embodiment.

Figure 18B:
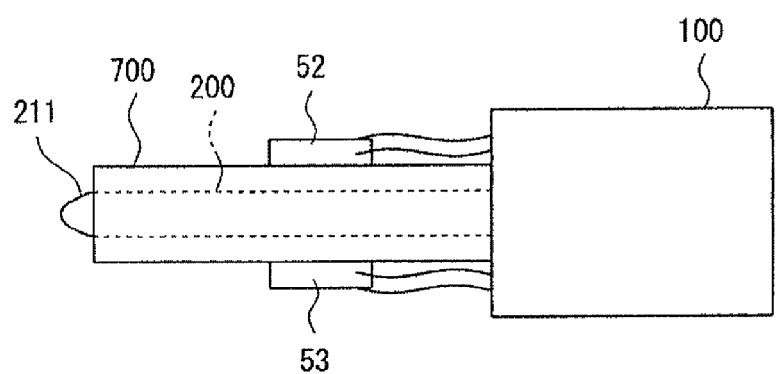
FIG. 18B shows an example of an attachment structure of the piezoelectric elements to the suction pipe.

In case of the fluid ejection device 3 having the suction pipe, the two piezoelectric elements 52 and are disposed and fixed to the outer circumferential surface of the suction pipe 700 at positions closer to the pulse generating unit 100 and opposed to each other with the pipe interposed therebetween similarly to the piezoelectric element 50 and the distortion gauge 51 in the second embodiment as illustrated in FIG. 18B.

The attachment structure of the piezoelectric elements 52 and 53 may be any of the attachment structure of the piezoelectric element 50 and the distortion gauge 51 shown in FIG. 13 and the structures shown in FIGS. 14A through 14D in the second embodiment.

The detailed structure of a drive unit 30" of the fluid ejection device 1 or 3 including the piezoelectric elements 52 and 53 for generating vibrating force and receiving vibration in this embodiment is now discussed with reference to FIG. 19.

Figure 19:
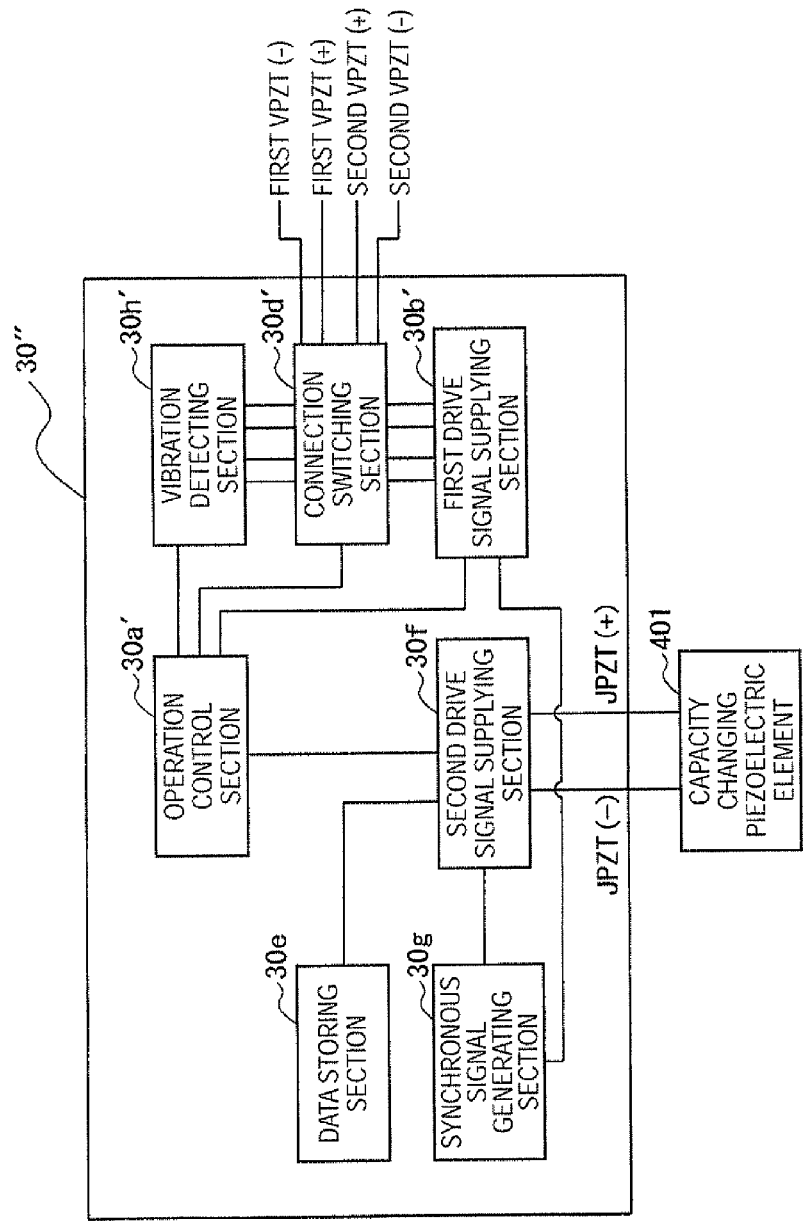
FIG. 19 is a block diagram showing a detailed structure of a drive unit.

FIG. 19 is a block diagram showing the detailed structure of the drive unit 30" according to this embodiment.

As shown in FIG. 19, the drive unit 30" includes an operation control section 30a', a first drive signal supplying section 30b', a vibration detecting unit 30h', a connection switching section 30d', the data storing section 30e, the second drive signal supplying section 30f, and the synchronous signal generating section 30g.

The operation control section 30a' has function of issuing operation commands to the respective components in response to operation input received from the input device of the fluid ejection device 1 or 3. More specifically, the operation control section 30a' has function of controlling various operation processes such as supplying drive signals from the first drive signal supplying section 30b', switching time divisions associated with the connection switching section 30d', determining contact condition of the nozzle 211 or the end of the suction pipe 700, and supplying drive signals from the second drive signal supplying section 30f based on the determination result.

The connection switching section 30d' switches between the electric connection between first supply line VPZT(−) and first supply line VPZT(+) of the piezoelectric element 52 and second supply line VPZT(−) and second supply line VPZT(+) of the piezoelectric element 53 and the vibration detecting section 30h, and the electric connection between the first supply line VPZT(−) and the first supply line VPZT(+) of the piezoelectric element 52 and the second supply line VPZT(−) and the second supply line VPZT(+) of the piezoelectric element 53 and the first drive signal supplying section 30b in response to control signals from the operation control section 30a'.

The connection may be switched by using a mechanical switch or switching elements such as transistors.

The vibration detecting section 30h' detects electromotive force generated by piezoelectric effect of the piezoelectric elements 52 and 53 having received the vibration of the connection flow path pipe 200 or the suction pipe 700, and outputs the electromotive force to the operation control section 30a' as detected voltage.

The flow of drive signal supply process to the piezoelectric elements 52 and 53 performed by the first drive signal supplying section 30b' is now discussed with reference to FIG. 20.

Figure 20:
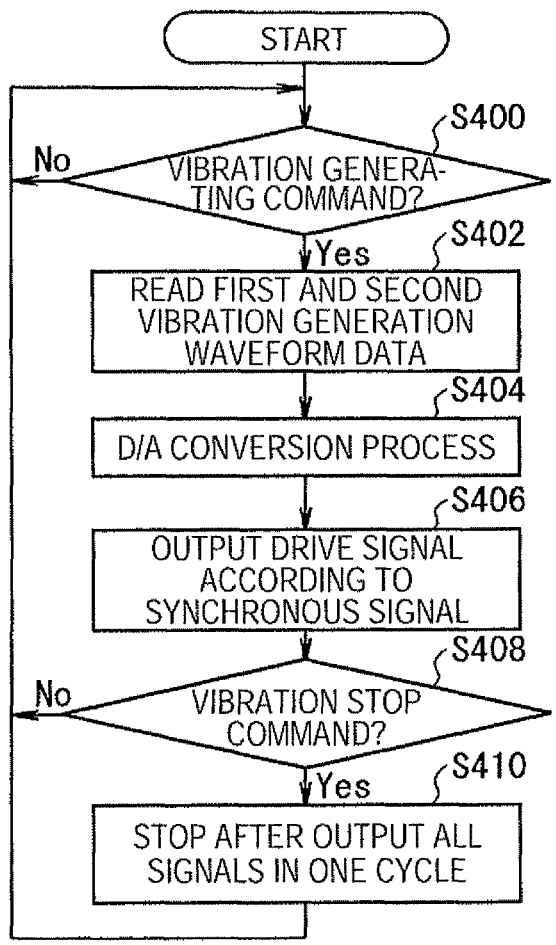
FIG. 20 is a flowchart showing drive signal supply process performed by a first drive signal supplying section.

FIG. 20 is a flowchart showing the drive signal supply process performed by the first drive signal supplying section 30b'.

When the process for supplying drive signals to the piezoelectric elements 52 and 53 is initiated under the dedicated program executed by the processor, the flow goes to step S400 as shown in FIG. 20.

In step S400, the first drive signal supplying section 30b' determines whether the vibration generating command is inputted from the operation control section 30a'. When it is determined that the vibration generating command is inputted (YES), the flow goes to step S402. When it is determined that the vibration generating command is not inputted (NO), the determination process is repeated until the command is inputted.

When the flow goes to step S402, the first drive signal supplying section 30b' reads waveform data for first vibration generation used for drive of the piezoelectric element 52 and waveform data for second vibration generation for drive of the piezoelectric element 53 from the data storing section 30e based on the identification information of the specified waveform contained in the vibration generating command. Then, the flow goes to step S404.

In step S404, the first drive signal supplying section 30b' converts the digital waveform signals of the first and second waveform data for vibration generation read in step S402 into analog waveform signals. Then, the flow goes to step S406.

In step S406, the first drive signal supplying section 30b' outputs drive signals for first vibration generation having the analog signal waveform obtained by the D/A conversion in step S404 in synchronization with synchronous signals from the synchronous signal generating section 30g to the piezoelectric element 52, and outputs drive signals for second vibration generation having the analog signal waveform obtained by the D/A conversion in step S404 in synchronization with synchronous signals from the synchronous signal generating section 30g to the piezoelectric element 53. Then, the flow goes to step S408.

In step S408, the first drive signal supplying section 30b' determines whether the vibration stop command is inputted from the operation control section 30a'. When it is determined that the vibration stop command is inputted (YES), the flow goes to step S410. When it is determined that the vibration stop command is not inputted (NO), the drive signal output process in step S404 is continued.

When the flow goes to step S410, the first drive signal supplying section 30b' stops drive signal supply to the piezoelectric elements 52 and 53 after output of all signals thereto in one cycle. Then, the flow goes to step S400.

The operation of the drive unit 30" according to this embodiment is now discussed.

The drive unit 30" in this embodiment controls supply contents of the drive signals to be supplied to the first drive signal supplying section 30b' in such a manner as to expand and contract the piezoelectric elements 52 and 53 disposed opposed to each other in the directions of increasing respective vibrating forces (expanding one of the piezoelectric elements 52 and 53 and contracting the other) to apply larger vibrating force.

When the drive switch of the WPS is turned on, the drive unit 30" alternately repeats the process for supplying drive signals to the piezoelectric elements 52 and 53 from the first drive signal supplying section 30b' for a given period and the process for detecting the level of vibration by the vibration detecting section 30h' for a given period by time division similarly to the third embodiment so as to perform both application of vibrating force and detection of the level of vibration generated by the applied vibrating force. Thus, the operation control section 30a' initially controls switching operation of the connection switching section 30d' by control signals.

More specifically, when the drive switch is turned on, the operation control section 30a' alternately switches between the electric connection between the first supply lines VPZT (−) and VPZT(+) and the second supply lines VPZT(−) and VPZT(+) and the first drive signal supplying section 30b' and the electric connection between the first supply lines VPZT (−) and VPZT(+) and the second supply lines VPZT(−) and VPZT(+) and the vibration detecting section 30h' by time division by controlling supply contents of control signals given to the connection switching section 30d'.

Simultaneously, the operation control section 30a' outputs vibration generating command to the first drive signal supplying section 30b' at the time of outputting the control signals to the connection switching section 30d'. By this step, the first supply lines VPZT(−) and VPZT (+) of the piezoelectric element 52 and the second supply lines VPZT(−) and VPZT (+) of the piezoelectric element 53 are electrically connected with the first drive signal supplying section 30b', and the vibration generating command is supplied to the first drive signal supplying section 30b'.

When receiving the vibration generating command from the operation control section 30a', the first drive signal supplying section 30b' reads waveform data for the first and second vibration generation from the data storing section 30e and supplies the data to the work memory such as RAM. Then, the first drive signal supplying section 30b' converts the digital waveform data read from the data storing section 30e into analog waveform signals.

Subsequently, the first drive signal supplying section 30b' outputs the drive signals for the first vibration generation thus generated to the piezoelectric element 52 and outputs the drive signals for the second vibration generation thus generated to the piezoelectric element 53 in synchronization with synchronous signals from the synchronous signal generating section 30g.

By this step, the piezoelectric elements 52 and expand and contract in the directions of increasing respective forces. For example, the piezoelectric element 53 contracts when the piezoelectric element 52 expands to produce expanding and contracting force (vibrating force). This vibrating force is transmitted to the connection flow path pipe 200 or the suction pipe 700 via the attachment portion to bend the connection flow path pipe 200 or the suction pipe 700 in the direction of applying the force thereto. The connection flow path pipe 200 or the suction pipe vibrates by the bending force and restoring force from the bended condition. In this case, larger vibration can be generated from smaller force by driving the piezoelectric elements 52 and 53 such that the applied vibrating force has the natural frequency of the connection flow path pipe 200 or the suction pipe 700.

After elapse of the given period during which the vibrating force is applied, the connection of the connection switching section 30d' is switched to the connection between the first supply lines VPZT(−) and VPZT(+) of the piezoelectric element 52 and the second supply lines VPZT(−) and VPZT(+) of the piezoelectric element 53 and the vibration detecting section 30h' in response to control signals from the operation control section 30a'. By this step, the given period after switching becomes the detection period by the vibration detecting section 30h'.

Thus, the vibration generating period and the vibration detecting period are alternately switched for each given period. In this case, vibration waveform having larger amplitude than that of the amplitude of the vibration waveform shown in FIG. 17A in the third embodiment can be generated by time division, and the level of vibration can be detected by time division.

According to this embodiment, both the electromotive forces of the piezoelectric elements 52 and 53 are detected as detection voltages. However, only one of the electromotive forces may be detected.

Moreover, the vibration detecting section 30h' may output the respective electromotive forces of the piezoelectric elements 52 and 53 to the operation control section 30a' as detected voltages. Alternatively, the vibration detecting section 30h' may calculate the average of the electromotive forces of the piezoelectric elements 52 and 53 and outputs the calculated average to the operation control section 30a' as the detected voltage.

The determination of the contact or non-contact of the nozzle 211 or the end of the suction pipe 700 by using the detected voltage is similar to that in the first through third embodiments except that the detected voltage is obtained by time division.

Other operations are similar to those performed by the operation control section 30a in the first through third embodiments, and the same explanation is not repeated herein.

Accordingly, the fluid ejection device 1 or 3 in this embodiment can expand and contract the two piezoelectric elements 52 and 53 in the directions of increasing respective vibrating forces.

By this method, larger vibrating force can be applied to the connection flow path pipe 200 or the suction pipe 700.

Moreover, application of vibrating force and detection of the level of the vibration generated by the vibrating force can be achieved by time division by using the piezoelectric elements 52 and 53.

Thus, the necessity for providing detection element such as distortion gauge for detecting the level of vibration is eliminated, and the component cost and processing cost associated with the detection element can be reduced.

According to the fourth embodiment, the nozzle 211 and the fluid ejection opening 212 correspond to a fluid ejection opening as referred to in any of the first, second, third, fourth and fourteenth aspects. The capacity changing section 405 and the second drive signal supplying section 30f correspond to a capacity changing unit as referred to in any of the first, third, thirteenth and fourteenth aspects. The fluid container 10 and the pump 20 correspond to a fluid supplying unit as referred to in any of the first and fourteenth aspects. The suction pipe 700 corresponds to a suction pipe as referred to in any of the third, sixth and seventh aspects. The suction pump 60 corresponds to a sucking force giving unit as referred to in the third aspect. The piezoelectric element 52, the piezoelectric element 53 and the first drive signal supplying section 30b' correspond to a vibrating unit as referred to in the twelfth aspect. The piezoelectric element 52, the piezoelectric element 53 and the vibration detecting section 30h' correspond to a vibration detecting unit as referred to in the eleventh aspect. The operation control section 30a' corresponds to an operation control unit as referred to in any of the first, thirteenth and fourteenth aspects. The operation control section 30a' and the connection switching section 30d' correspond to a time division control unit as referred to in the eleventh aspect. The vibration detecting section 30h' corresponds to an electromotive force detecting section as referred to in the eleventh aspect. The piezoelectric elements 52 and 53 correspond to a vibrating force generating section as referred to in the twelfth aspect.

According to the first and second embodiments, the vibration receiving section is constituted by the metal resistor type distortion gauge 51 having resistor formed by resistance line or photo-etched resistance foil. However, the vibration receiving section may be formed by a distortion gauge of other system such as semiconductor system, piezoelectric element system, surface elastic wave system, magneto-distortion system, and optical fiber system.

According to the first through fourth embodiments, the vibrating force generating unit is constituted by piezoelectric element. However, the vibrating force generating unit may be formed by a component generating other vibrating force such as solenoid and motor.

According to the first and second embodiments, the piezoelectric element 50 and the distortion gauge 51 are fixed to positions opposed to each other with the pipe interposed therebetween. However, the piezoelectric element 50 and the distortion gauge 51 may be disposed at other positions as long as vibration can be generated and received.

According to the first through fourth embodiments, the piezoelectric elements 50, 52 and 53 and the distortion gauge 51 are disposed on the outer circumferential surface of the connection flow path pipe 200 or the suction pipe 700 at positions closer to the pulse generating unit 100 and opposed to each other with interposed between the piezoelectric elements 50, 52 and the distortion gauge 51. However, the piezoelectric elements 50, 52 and 53 and the distortion gauge 51 may be located at other positions. For example, these components may be disposed closer to the end of the connection flow path pipe 200 or the suction pipe 700 or on the inner side of the pipe rather than on the outer circumferential surface of the pipe.

According to the fourth embodiment, larger vibration is generated by using the two piezoelectric elements 52 and 53. However, vibrating force (generated vibration) may be increased by using three or more piezoelectric elements.

The first through fourth embodiments and the modified examples described herein are preferred specific examples of the invention to which various preferable limitations in technical view are imposed. However, the scope of the invention is not limited to these examples as long as any particular limitations to the invention are not specified. The figures used in this specification are only schematic figures having horizontal and vertical reduction scales different from the actual ones for the components and parts to simplify the explanation.

The invention is not limited to the first through fourth embodiments and the modified examples described herein. It is thus intended that modifications, improvements and the like without departing from the scope of the invention are included in the appended claims.

What is claimed is:

1. A fluid ejection device comprising:
a fluid chamber whose capacity is variable;
an inlet flow path and an outlet flow path communicating with the fluid chamber;
a capacity changing unit which changes the capacity of the fluid chamber, the capacity changing unit including a piezoelectric element;
a fluid supplying unit which supplies fluid to the inlet flow path;
a nozzle including a fluid ejection opening disposed at an end of the outlet flow path opposite to an end communicating with the fluid chamber;
a vibrating unit which vibrates a component in the vicinity of the fluid ejection opening;
a vibration detecting unit including a sensor which detects the level of vibration of the nozzle in the vicinity of the fluid ejection opening; and
an operation control unit which supplies drive signals that control operation of the capacity changing unit based on the level of the vibration detected by the vibration detecting unit, the drive signals causing the piezoelectric element to expand or contract to change the capacity of the fluid chamber.

2. The fluid ejection device according to claim 1, wherein the nozzle in the vicinity of the fluid ejection opening forms the fluid ejection opening.

3. The fluid ejection device according to claim 1, further comprising:
a suction pipe having a suction opening positioned in the vicinity of the fluid ejection opening and a passage through which an object sucked via the suction opening passes; and
a sucking force giving unit which gives sucking force for sucking the object in the vicinity of the suction opening, wherein the component in the vicinity of the fluid ejection opening forms the suction opening.

4. The fluid ejection device according to claim 1, wherein:
the vibrating unit has a vibrating force generating section which generates vibrating force for vibrating the fluid ejection opening;

the vibration detecting unit has a vibration receiving section which receives vibration; and the vibrating force generating section and the vibration receiving section are provided on the outlet flow path.

5. The fluid ejection device according to claim 4, wherein:

a flat surface is provided at least on a part of the outer circumferential surface of the outlet flow path; and the vibrating force generating section and the vibration receiving section are provided on the flat surface.

6. The fluid ejection device according to claim 3, wherein:

the vibrating unit has a vibrating force generating section which generates vibrating force for vibrating the suction opening;

the vibration detecting unit has a vibration receiving section which receives vibration; and the vibrating force generating section and the vibration receiving section are provided on the suction pipe.

7. The fluid ejection device according to claim 6, wherein:

a flat surface is provided at least on a part of the outer circumferential surface of the suction pipe; and the vibrating force generating section and the vibration receiving section are provided on the flat surface.

8. The fluid ejection device according to claim 4, wherein the vibration receiving section has a distortion gauge.

9. The fluid ejection device according to claim 4, wherein the vibrating force generating section has a vibrating force generating piezoelectric element.

10. The fluid ejection device according to claim 9, wherein the vibrating force generating section has function of generating vibrating force and function of receiving vibration as the vibration receiving section by using the vibrating force generating piezoelectric element for generating vibrating force.

11. The fluid ejection device according to claim 10, wherein:

the vibrating unit has a drive section which drives the vibrating force generating piezoelectric element;

the vibration detecting unit has an electromotive force detecting section which detects electromotive force generated on the vibrating force generating piezoelectric element; and a time division control unit which controls the drive section and the electromotive force detecting section such that supply of drive signals by the drive section and detection of electromotive force by the electromotive force detecting section are performed by time division is provided.

12. The fluid ejection device according to claim 4, wherein:

the vibrating unit has the plural vibrating force generating sections; and the vibrating unit controls operations of the vibrating force generating sections such that forces generated by the plural vibrating force generating sections can increase the vibrating force.

13. The fluid ejection device according to claim 1, wherein the operation control unit allows operation of the capacity changing unit when the level of vibration detected by the vibration detecting unit is lower than a predetermined level, and prohibits operation of the capacity changing unit when the level of the vibration is equal to or higher than the predetermined level.

14. An operating instrument which supports medical treatment for an affected portion by using ejection of fluid, comprising the fluid ejection device according to claim 1.

15. A driving method of a fluid ejection device comprising:

the fluid ejection device including:

a fluid chamber whose capacity is variable, an inlet flow path and an outlet flow path communicating with the fluid chamber, a capacity changing unit which changes the capacity of the fluid chamber, the capacity changing unit including a piezoelectric element, a fluid supplying unit which supplies fluid to the inlet flow path, a nozzle including a fluid ejection opening disposed at an end of the outlet flow path opposite to an end communicating with the fluid chamber, a vibrating unit, a vibration detecting unit including a sensor, and an operation control unit;

the method comprising:

vibrating a component in the vicinity of the fluid ejection opening by the vibrating unit;

detecting the level of vibration of the nozzle in the vicinity of the fluid ejection opening by the vibration detecting unit; and supplying drive signals that control operation of the capacity changing unit based on the level of the vibration detected in the vibration detecting step by the operation control unit, the drive signals causing the piezoelectric element to expand or contract to change the capacity of the fluid chamber.

* * * * *